(12) United States Patent
Yotani et al.

(10) Patent No.: US 10,550,426 B2
(45) Date of Patent: Feb. 4, 2020

(54) METHOD FOR DETECTING METHYLATED DNA

(71) Applicants: SEKISUI MEDICAL CO., LTD., Chuo-ku (JP); MIE UNIVERSITY, Tsu-shi (JP)

(72) Inventors: Takuya Yotani, Ibaraki (JP); Tsutomu Nobori, Mie (JP)

(73) Assignees: SEKISUI MEDICAL CO., LTD., Chuo-ku (JP); MIE UNIVERSITY, Tsu-shi (JP)

(\*) Notice: Subject to any disclaimer, the term of this patent is extended or adjusted under 35 U.S.C. 154(b) by 821 days.

(21) Appl. No.: 14/771,936

(22) PCT Filed: Mar. 7, 2014

(86) PCT No.: PCT/JP2014/055923
§ 371 (c)(1),
(2) Date: Dec. 14, 2015

(87) PCT Pub. No.: WO2014/136930
PCT Pub. Date: Sep. 12, 2014

(65) Prior Publication Data
US 2016/0138097 A1 May 19, 2016

(30) Foreign Application Priority Data

Mar. 7, 2013 (JP) .................. 2013-045845
Mar. 28, 2013 (JP) .................. 2013-067814
Jul. 18, 2013 (JP) .................. 2013-149867
Feb. 28, 2014 (WO) .................. PCT/JP2014/055155

(51) Int. Cl.
| | | |
|---|---|---|
| *C12Q 1/68* | (2018.01) | |
| *C12Q 1/6848* | (2018.01) | |
| *C12Q 1/686* | (2018.01) | |
| *C12Q 1/6827* | (2018.01) | |
| *G01N 30/96* | (2006.01) | |

(52) U.S. Cl.
CPC .......... *C12Q 1/6848* (2013.01); *C12Q 1/686* (2013.01); *C12Q 1/6827* (2013.01); *G01N 30/96* (2013.01)

(58) Field of Classification Search
None
See application file for complete search history.

(56) References Cited

U.S. PATENT DOCUMENTS

| | | |
|---|---|---|
| 5,786,146 A | 7/1998 | Herman et al. |
| 2005/0064428 A1 | 3/2005 | Berlin |
| 2014/0030713 A1 | 6/2014 | Yotani et al. |

FOREIGN PATENT DOCUMENTS

| | | |
|---|---|---|
| JP | 2005-514035 A | 5/2005 |
| WO | WO 03/057909 A2 | 7/2003 |
| WO | 2012/108516 A1 | 8/2012 |

OTHER PUBLICATIONS

Pedersen et al. (BMC Molecular Biology 2012, 13:12, p. 1-8).\*
El-Maari et al. (Nucleic Acids Research, 2002, 30(6):e25, p. 1-4) (Year: 2002).\*
Hoogendorn et al. (Hum Genet, 1999, 104:89-93) (Year: 1999).\*
Extended European Search Report dated Sep. 29, 2016 in Patent Application No. 14761083.6.
Maryam M. Matin, et al., "An Analytical Method for the Detection of Methylation Differences at Specific Chromosomal Loci Using Primer Extension and Ion Pair Reverse Phase HPLC", Human Mutation, vol. 20, 2002, XP-002761739, pp. 305-311.
P. Couvert et al., "DHPLC-Based Method for DNA Methylation Analysis of Differential Methylated Regions from Imprinted Genes", BioTechniques, 2003, vol. 34, No. 2, pp. 356 to 362.
Kevin K. Divine et al., "Nested multigene MSP/ DHPLC method for analyzing promoter hypermethylation status in clinical samples", BioTechniques, 2006, vol. 40, No. 1, pp. 40 to 46.
James G. Herman et al., "Methylation-specific PCT: A novel PCR assay for methylation status of CpG islands", Proc. National Academy of Sciences, Sep. 1996, vol. 93, pp. 9821-9826.
Ramin Sadri et al., "Rapid analysis of DNA methylation using new restriction enzyme sites created by bisutfite modification", *Nucleic Acids Research*, 1996, vol. 24, No. 24, pp. 5058-5059.
Zhenggang Xiong et al., "COBRA: a sensitive and quantitative DNA methylation assay", *Nucleic Acids Research*, 1997, vol. 25, No. 12, pp. 2532-2534.
International Search Report and Written Opinion dated May 13, 2014 for PCT/JP2014/055923 filed on Mar. 7, 2014.
Combined Office Action and Search Report dated Jun. 21, 2016 in Chinese Patent Application No. 201480018778.3 (with English translation of category of cited documents).
Yan Jin, et al "Application and assessment of MSP-DHPLC technology in detection of MGMT gene methylation", J. Mol. Diagn. Ther., vol. 3, No. 1, Jan. 6, 2011, pp. 6-9.

\* cited by examiner

*Primary Examiner* — Stephanie K Mummert
(74) *Attorney, Agent, or Firm* — Oblon, McClelland, Maier & Neustadt, L.L.P.

(57) ABSTRACT

Provided is a rapid and simple method of detecting methylated DNA. The method of detecting methylated DNA includes the following steps of: (1) treating sample DNA with a hydrogen sulfite; (2) amplifying the sample DNA treated with the hydrogen sulfite by PCR; and (3) subjecting the resultant PCR amplification product to ion-exchange chromatography.

14 Claims, 10 Drawing Sheets

Specification includes a Sequence Listing.

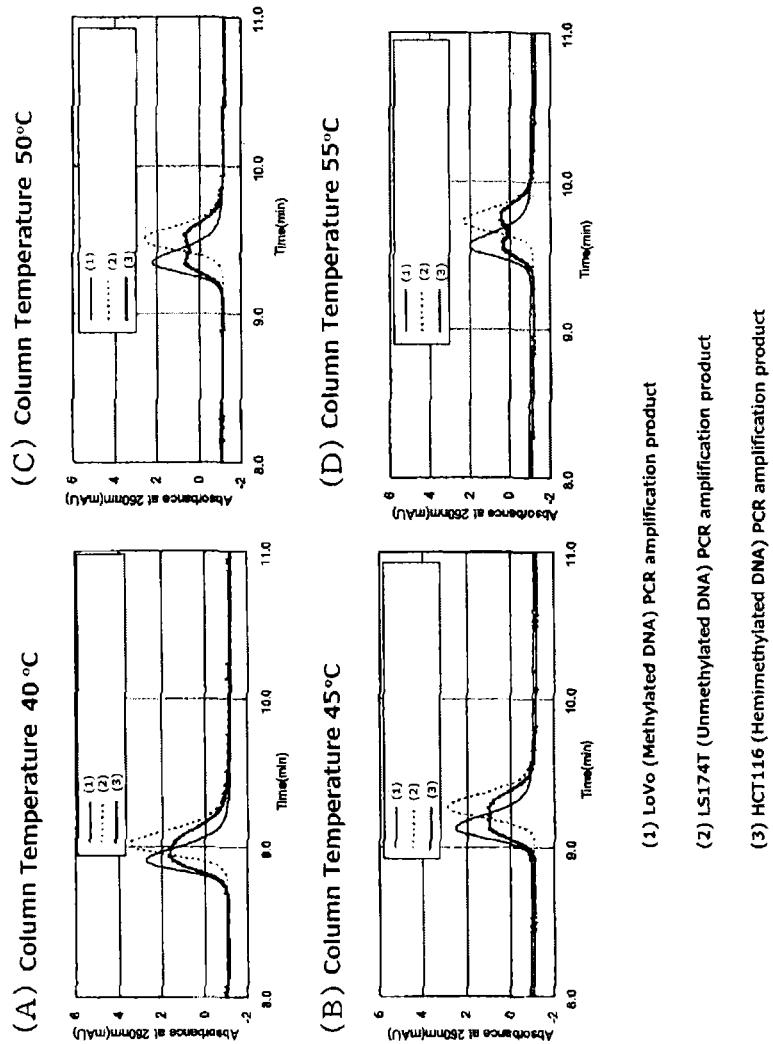

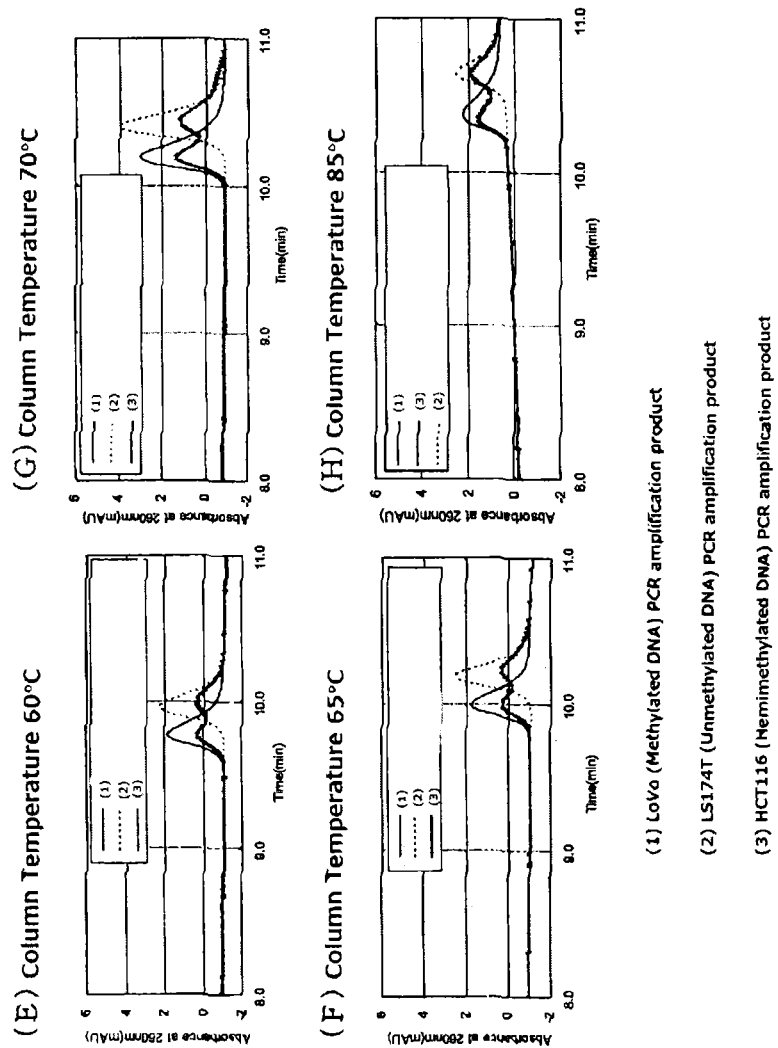

METHOD FOR DETECTING METHYLATED DNA

FIELD OF THE INVENTION

The present invention relates to a method of detecting methylated DNA, and more specifically, to a rapid and simple method of detecting methylated DNA through ion-exchange chromatographic assay of a PCR-amplified product of DNA treated with a hydrogen sulfite.

BACKGROUND OF THE INVENTION

In recent years, epigenetics has been recognized as being involved in various biological phenomena, and research concerning epigenetic analysis has been actively conducted. In particular, it has been revealed that aberrant methylation of DNA is deeply involved in canceration, and this fact has been attracting attention. As a characteristic epigenetic aberration in cancer cells, there is known aberrant DNA methylation of CpG islands in promoter regions of some genes. The CpG island refers to a region in which a two-nucleotide sequence of cytosine (C) and guanine (G) linked through a phosphodiester bond (p) occurs at a high frequency, and the CpG island is often present in a promoter region upstream of a gene. The aberrant DNA methylation of the CpG island is involved in carcinogenesis through, for example, inactivation of a tumor suppressor gene. Canceration is induced by inactivation of various tumor suppressor genes such as CDKN2A, CDH1, MLH1, RB, BRCA1, TSLC1, and RUNX3, through aberrant methylation of CpG islands present in their promoter regions. When DNA is methylated, the methylated DNA is replicated at the time of cell division and passed on to daughter cells. Accordingly, when a tumor suppressor gene is inactivated by aberrant methylation, the tumor suppressor gene continues to be in the inactivated state.

As an already established analysis method for methylated DNA, there is known a method involving utilizing a hydrogen sulfite (bisulfite) reaction. This method is the most generally used method for analysis of methylated DNA. When single-stranded DNA is treated with the hydrogen sulfite, cytosine is converted to uracil through sulfonation, hydrolytic deamination, and desulfonation. On the other hand, methylated cytosine has an extremely low reaction rate in the sulfonation that occurs first, and hence remains as methylated cytosine in a reaction time of the hydrogen sulfite treatment to be actually performed. Therefore, when a polymerase chain reaction (PCR) is performed using the DNA treated with the hydrogen sulfite, methylated cytosine remains as cytosine, whereas unmethylated cytosine is amplified as thymine in place of uracil. The base difference between cytosine and thymine, which occurs in a sequence of a PCR amplification product, is utilized to analyze a methylation status. Generally used methods that adopt the foregoing as their basic principle are a methylation-specific PCR (MSP) method described in Patent Document 1 and Non Patent Document 1, and a combined bisulfite restriction analysis (COBRA) method described in Non Patent Documents 2 and 3.

The MSP method is a method involving, after the hydrogen sulfite treatment of DNA, performing PCR amplification with a methylated sequence-specific primer and a unmethylated sequence-specific primer, and agarose gel electrophoresis in the stated order, and determining a DNA methylation status of a region of interest based on the presence or absence of amplification products obtained with both the primers. The COBRA method is a method involving, after the hydrogen sulfite treatment of DNA, performing PCR amplification with a primer common to methylated DNA and unmethylated DNA, treatment with a restriction enzyme that recognizes a site of a sequence difference between methylated DNA and unmethylated DNA, and agarose gel electrophoresis in the stated order, and determining a DNA methylation status of a region of interest based on the presence or absence of a restriction enzyme-treated fragment. Both the methods are still widely used methods because the methods allow quantitative analysis of methylated DNA without any special apparatus. However, there has been a problem in that those methods take time and effort in the analysis owing to the utilization of the electrophoresis method.

Meanwhile, for separation assay of biopolymers such as nucleic acids, proteins, and polysaccharides in the fields of biochemistry, medicine, and the like, ion-exchange chromatography is generally used as a method that allows accurate detection to be performed simply and within a short period of time. The ion-exchange chromatography is a method of separating a substance as a measurement object through the utilization of an electrostatic interaction occurring between an ion-exchange group of a column packing material and an ionic group in the substance as the measurement object. One type of this method is based on anion exchange and another is based on cation exchange. The anion-exchange chromatography allows an anionic substance to be separated through the use of a column packing material having a cationic functional group as the ion-exchange group. In addition, the cation-exchange chromatography allows a cationic substance to be separated through the use of a column packing material having an anionic functional group as the ion-exchange group.

In separation of PCR amplification products of nucleic acids using the ion-exchange chromatography, use is generally made of the anion-exchange chromatography that performs the separation by utilizing negative charge of phosphate contained in a nucleic acid molecule. The cationic functional group of the column packing material in the anion-exchange chromatography is classified into a weak cationic group such as a diethylaminoethyl group, and a strong cationic group such as a quaternary ammonium group. Columns packed with column packing materials having those cationic functional groups as the ion-exchange groups are already commercially available, and used in various fields of research.

In addition, one of the inventors of the present invention developed, as a column packing material for ion-exchange chromatography, a column packing material having both a strong cationic group and a weak cationic group as cationic functional groups of the column packing material, and reported separation assay of a single-base difference between 20-mer unmethylated synthetic oligonucleotides by ion-exchange chromatography using a column packed with this packing material (Patent Document 2).

CITATION LIST

Patent Document

Patent Document 1: U.S. Pat. No. 5,786,146 B2
Patent Document 2: WO 2012/108516 A1

Non Patent Document

Non-Patent Document 1: Proc. Natl. Acad. Sci. USA, 93, 9821-9826 (1996)

Non-Patent Document 2: Nucleic Acids Res., 24, 5058-5059 (1996)

Non-Patent Document 3: Nucleic Acids Res., 25, 2532-2534 (1997)

SUMMARY OF THE INVENTION

Problem to be Solved by the Invention

When cancer risk assessment is performed based on DNA methylation analysis utilizing the hydrogen sulfite reaction as described above, in order to perform earlier or more precise assessment, a difference in DNA nucleotide sequence resulting from the hydrogen sulfite reaction needs to be accurately detected. An object of the present invention is to provide a rapid and simple method of detecting methylated DNA, in which the time and effort required in analysis by electrophoresis is eliminated. Specifically, an object of the present invention is to provide a method that is excellent in separation performance for a detection signal so as to allow highly accurate and highly sensitive detection of DNA methylation.

Solution to the Problem

The inventors of the present invention found that methylated DNA was able to be detected rapidly and simply when PCR amplification products obtained through the amplification of DNA treated with a hydrogen sulfite by PCR were separated by ion-exchange chromatography. The inventors of the present invention then further conducted extensive investigations on assay conditions for the ion-exchange chromatography. As a result, the inventors surprisingly found that peak separation of a detection signal of methylated DNA was dramatically improved in a manner dependent on a column temperature in the ion-exchange chromatography. Thus, the inventors completed the present invention.

The present invention has the following constructions.

[1] A method of detecting methylated DNA, comprising the following steps (1), (2), and (3):
  (1) treating sample DNA with a hydrogen sulfite;
  (2) amplifying the sample DNA treated with the hydrogen sulfite by PCR; and
  (3) subjecting the resultant PCR amplification product to ion-exchange chromatography.

[2] A method of detecting methylated DNA, comprising the following steps (1), (2), and (3'):
  (1) treating sample DNA with a hydrogen sulfite;
  (2) amplifying the sample DNA treated with the hydrogen sulfite by PCR; and
  (3') subjecting the resultant PCR amplification product to ion-exchange chromatography at a column temperature of 45° C. or more and less than 90° C.

[3] The method according to [1] or [2], in which the ion-exchange chromatography comprises anion-exchange chromatography.

[4] The method according to any one of [1] to [3], in which a column packing material to be used in the ion-exchange chromatography contains base particles each having both a strong cationic group and a weak cationic group on a surface thereof on its surface.

[5] The method according to any one of [1] to [4], in which an eluent to be used in elution of the PCR amplification product in the ion-exchange chromatography contains an antichaotropic ion.

[6] The method according to any one of [1] to [5], in which the antichaotropic ion comprises any one or both of a sulfate ion and an ammonium ion.

[7] The method according to any one of [1] to [6], further comprising the step of comparing a detection signal obtained in the ion-exchange chromatography of the PCR amplification product of the sample DNA treated with the hydrogen sulfite to a detection signal obtained in ion-exchange chromatography of:
  a PCR amplification product of DNA treated with the hydrogen sulfite, the DNA being identical in nucleotide sequence to the sample DNA but being free of methylation; or
  a PCR amplification product of DNA treated with the hydrogen sulfite, the DNA being identical in nucleotide sequence to the sample DNA and having a predetermined proportion of methylation.

[8] The method according to [7], further comprising the step of measuring, based on results of the comparing step, presence or absence, a methylation ratio, or a presence ratio of methylated DNA in the sample DNA.

[9] The method according to any one of [1] to [6], further comprising the step of subtracting a detection signal obtained in ion-exchange chromatography of a PCR amplification product of DNA treated with the hydrogen sulfite, the DNA being identical in nucleotide sequence to the sample DNA but being free of methylation from a detection signal obtained in the ion-exchange chromatography of the PCR amplification product of the sample DNA treated with the hydrogen sulfite to obtain differential data.

[10] The method according to [9], further comprising the step of measuring, based on the differential data, presence or absence, a methylation ratio, or a presence ratio of methylated DNA in the sample DNA.

[11] A method of extracting a signal of methylated DNA from a signal of sample DNA, the method comprising the following steps (1) to (6):
  (1) treating sample DNA with a hydrogen sulfite;
  (2) amplifying the sample DNA treated with the hydrogen sulfite by PCR;
  (3) subjecting a PCR amplification product obtained in the step (2) to ion-exchange chromatography;
  (4) treating DNA that is identical in nucleotide sequence to the sample DNA but is free of methylation with the hydrogen sulfite, followed by PCR amplification;
  (5) subjecting a PCR amplification product obtained in the step (4) to ion-exchange chromatography; and
  (6) subtracting a detection signal in chromatography obtained in the step (5) from a detection signal in chromatography obtained in the step (3) to obtain differential data.

[12] A use, for detection of methylated DNA, of a column for ion-exchange chromatography packed with a column packing material that contains base particles each having both a strong cationic group and a weak cationic group on a surface thereof on its surface.

[13] A use, for detection of methylated DNA, of an eluent for ion-exchange chromatography containing an antichaotropic ion.

Effects of the Invention

According to one embodiment of the present invention, the method of detecting methylated DNA involving utilizing ion-exchange chromatography is provided. The ion-exchange chromatography to be performed in the method according to the one embodiment of the present invention is excellent in peak separation between detection signals of methylated DNA and unmethylated DNA, and allows accurate detection of methylated DNA. Therefore, according to the one embodiment of the present invention, the rapid and simple, and highly accurate method of detecting methylated DNA that does not require the time and effort as required in the electrophoresis method is provided. The method of detecting methylated DNA according to the one embodiment of the present invention is useful for a clinical examination such as a cancer risk examination.

BRIEF DESCRIPTION OF THE DRAWINGS

FIGS. 4-1 are chromatograms of PCR amplification products (136 bp) of methylated DNA and unmethylated DNA each treated with a hydrogen sulfite, the DNAs being derived from the CDKN2A gene promoter, when the PCR amplification products are assayed with the anion exchange column obtained in Reference Example 1 at column temperatures of from 40° C. to 85° C.

FIGS. 4-2 are chromatograms of PCR amplification products (136 bp) of methylated DNA and unmethylated DNA each treated with a hydrogen sulfite, the DNAs being derived from the CDKN2A gene promoter, when the PCR amplification products are assayed with the anion exchange column obtained in Reference Example 1 at column temperatures of from 40° C. to 85° C.

FIGS. 5-1 are chromatograms of PCR amplification products (77 bp) of methylated DNA and unmethylated DNA each treated with a hydrogen sulfite, the DNAs being derived from the CDKN2A gene promoter, when the PCR amplification products are assayed with the anion exchange column obtained in Reference Example 1 at column temperatures of from 40° C. to 85° C.

FIGS. 5-2 are chromatograms of PCR amplification products (77 bp) of methylated DNA and unmethylated DNA each treated with a hydrogen sulfite, the DNAs being derived from the CDKN2A gene promoter, when the PCR amplification products are assayed with the anion exchange column obtained in Reference Example 1 at column temperatures of from 40° C. to 85° C.

FIGS. 7-1 are chromatograms for showing a DNA methylation ratio-dependent variation in chromatography elution time. FIG. 7-1A is a chromatogram of DNAs having different DNA methylation ratios (0%, 25%, 50%, 75%, and 100%) and FIG. 7-1B is a chromatogram of 50% methylated DNAs having different DNA methylation sites (random, near the 5' side, near the 3' side, and central).

FIG. 7-2 is a plot for showing a DNA methylation ratio-dependent variation in chromatography elution time. FIG. 7-2C is a plot of elution time versus DNA methylation ratio.

DESCRIPTION OF THE EMBODIMENTS

Figure 1:
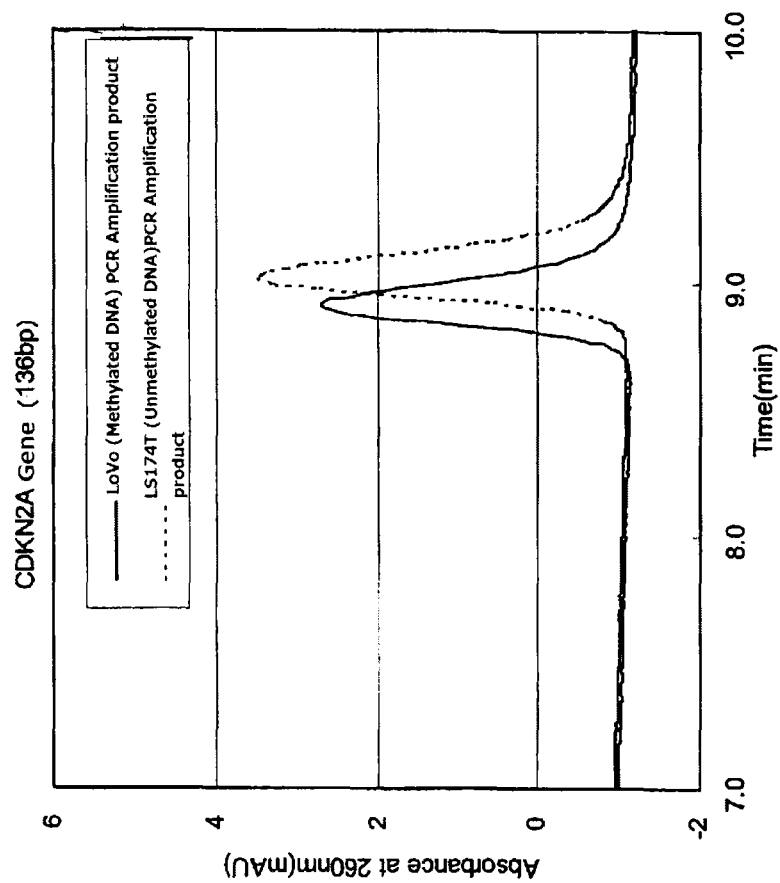
FIG. 1 is a chromatogram of PCR amplification products (136 bp) of methylated DNA and unmethylated DNA derived from a CDKN2A gene promoter, using an anion exchange column obtained in Reference Example 1.

In the present invention, as sample DNA to be subjected to the detection of methylated DNA, there is given DNA of any organism, including animals, plants, and microorganisms. Of those, DNA of an animal is preferred, and DNA of a mammal is more preferred. Examples of the mammal include, but are not limited to, humans, monkeys, mice, rats, guinea pigs, rabbits, sheep, goats, horses, cattle, pigs, dogs, and cats. The sample DNA may be obtained from an organism-derived sample containing DNA, through extraction, isolation, or purification.

Examples of the organism-derived sample containing the sample DNA include: various cells harvested from the above-mentioned organism, such as tissue cells, blood cells, or cells present in urine, feces, saliva, or any other body fluid or secretion; and cultured cell lines derived from the above-mentioned organisms. Further, the organism-derived sample also encompasses cells characteristic of various diseases (such as solid cancers and leukemia).

A method for the extraction, isolation, or purification of the sample DNA from the organism-derived sample is not particularly limited, and a known technique may be appropriately selected and used. As a known method for the preparation of the sample DNA, there are given, for example, a phenol chloroformmethod, and DNA extraction methods using commercially available DNA extraction kits such as QIAamp DNA Mini kit (manufactured by Qiagen), Clean Columns (manufactured by NexTec), AquaPure (manufactured by Bio-Rad), ZR Plant/Seed DNA Kit (manufactured by Zymo Research), prepGEM (manufactured by ZyGEM), and BuccalQuick (manufactured by TrimGen) to be described later.

In the method of detecting methylated DNA of the present invention, the sample DNA extracted from the organism-derived sample is treated with a hydrogen sulfite. A method for the hydrogen sulfite treatment of DNA is not particularly limited, and a known technique may be appropriately selected and used. As a known method for the hydrogen sulfite treatment, there are given, for example, methods using commercially available kits such as EpiTect Bisulfite Kit (48) (manufactured by Qiagen) to be described later, MethylEasy (manufactured by Human Genetic Signatures Pty), Cells-to-CpG Bisulfite Conversion Kit (manufactured by Applied Biosystems), and CpGenome Turbo Bisulfite Modification Kit (manufactured by MERCK MILLIPORE).

Next, the sample DNA treated with the hydrogen sulfite is amplified by PCR. A method for the PCR amplification is not particularly limited, and a known technique may be appropriately selected and used depending on, for example, the sequence, length, and amount of the DNA to be amplified. The chain length of the PCR amplification product may be appropriately decided in consideration of factors such as the shortening of the amplification time of the PCR, and the shortening of assay time and maintenance of separation performance in the ion-exchange chromatography. For example, the chain length of the PCR amplification product in the case of using sample DNA containing a large CpG island is preferably 1,000 bp or less, more preferably 700 bp or less, even more preferably 500 by or less. On the other hand, the chain length of the PCR amplification product in the case of using sample DNA containing a small CpG island has a lower limit of from 30 bp to 40 bp, which is the chain length of a PCR amplification product in the case of using an around 15-mer primer capable of avoiding non-specific hybridization in PCR. In this regard, however, it is preferred to design a primer so that the content of the CpG island may be rich. For example, the content of cytosines of CpG sites is preferably 2% or more, more preferably 5% or more with respect to the chain length of the PCR amplification product.

When DNA is treated with the hydrogen sulfite, unmethylated cytosine in the DNA is converted to uracil, whereas methylated cytosine remains as cytosine. When the DNA treated with the hydrogen sulfite is amplified by PCR, uracil derived from unmethylated cytosine is further replaced by thymine, causing the presence ratio between cytosine and thymine to differ between methylated DNA and unmethylated DNA. In the method of detecting methylated DNA of the present invention, the difference in presence ratio between the bases is utilized to analyze the methylation status of DNA.

Next, the resultant PCR amplification product is subjected to ion-exchange chromatography. The ion-exchange chromatography to be performed in the present invention is suitably anion-exchange chromatography. A column packing material to be used in the ion-exchange chromatography to be performed in the present invention is not particularly limited as long as the column packing material consists of base particles each having a strong cationic group on the surface. However, base particles each having both a strong cationic group and a weak cationic group on the surface of the packing material, which are disclosed in Patent Document 2, are preferred.

Herein, the strong cationic group means a cationic group that dissociates in a wide pH range of from 1 to 14. That is, the strong cationic group can keep its dissociated (cationized) state without being influenced by the pH of an aqueous solution.

An example of the strong cationic group is a quaternary ammonium group. Specific examples thereof include trialkylammonium groups such as a trimethylammonium group, a triethylammonium group, and a dimethylethylammonium group. In addition, as a counter ion of the strong cationic group, there are given, for example, halide ions such as a chloride ion, a bromide ion, and an iodide ion.

The amount of the strong cationic group to be introduced to the surface of each of the base particles is not particularly limited, but has a preferred lower limit of 1 µeq/g and a preferred upper limit of 500 µeq/g, with respect to the dry weight of the packing material. When the amount of the strong cationic group is less than 1 µeq/g, retention ability is weak and separation performance may be deteriorated. When the amount of the strong cationic group is more than 500 µeq/g, the retention ability becomes so strong that the PCR amplification product cannot be easily eluted, resulting in a problem such as an excessively long assay time in some cases.

Herein, the weak cationic group means a cationic group having a pka of 8 or more. That is, the dissociation state of the weak cationic group changes owing to the influence of the pH of an aqueous solution. That is, when the pH becomes more than 8, a proton of the weak cationic group is dissociated to increase the ratio of groups having no positive charge. Conversely, when the pH becomes less than 8, the weak cationic group is protonated to increase the ratio of groups having positive charge.

Examples of the weak cationic group include a tertiary amino group, a secondary amino group, and a primary amino group. Of those, a tertiary amino group is desirable.

The amount of the weak cationic group to be introduced to the surface of each of the base particles is not particularly limited, but has a preferred lower limit of 0.5 µeq/g and a preferred upper limit of 500 µeq/g, with respect to the dry weight of the packing material. When the amount of the weak cationic group is less than 0.5 µeq/g, which is too small, separation performance may not be improved. When the amount of the weak cationic group is more than 500 µeq/g, as in the case of the strong cationic group, the retention ability becomes so strong that the PCR amplification product cannot be easily eluted, resulting in a problem such as an excessively long assay time in some cases.

The amount of the strong cationic group or weak cationic group on the surface of each of the base particles may be measured by quantifying nitrogen atoms contained in amino groups. As a method of quantifying nitrogen, for example, the Kjeldahl method is given. In the case of the packing material described in the present invention (Examples), first, nitrogen contained in the strong cationic group after polymerization is quantified, and then nitrogen contained in the strong cationic group and weak cationic group after the introduction of the weak cationic group is quantified. Thus, the amount of the weak cationic group introduced later can be calculated. Through such quantification, the amount of the strong cationic group and the amount of the weak cationic group can be adjusted to fall within the above-mentioned ranges in the preparation of the packing material.

As the base particles, for example, synthetic polymer fine particles obtained by using a polymerizable monomer and the like or inorganic fine particles such as silica-based fine particles may be used. Of those, hydrophobic cross-linked polymer particles formed of a synthetic organic polymer are desirable.

The hydrophobic cross-linked polymer may be any of: a hydrophobic cross-linked polymer obtained by copolymerizing at least one kind of hydrophobic cross-linkable monomer and at least one kind of monomer having a reactive functional group; and a hydrophobic cross-linked polymer obtained by copolymerizing at least one kind of hydrophobic cross-linkable monomer, at least one kind of monomer having a reactive functional group, and at least one kind of hydrophobic cross-linkable monomer.

The hydrophobic cross-linkable monomer is not particularly limited as long as the monomer is a monomer having two or more vinyl groups per monomer molecule, and examples thereof include: di(meth)acrylic acid esters such as ethylene glycol di(meth)acrylate, polyethylene glycol di(meth)acrylate, propylene glycol di(meth)acrylate, and polypropylene glycol di(meth)acrylate, tri(meth)acrylic acid esters or tetra(meth)acrylic acid esters such as trimethylolmethane tri(meth)acrylate and tetramethylolmethane tri(meth)acrylate; and aromatic compounds such as divinylbenzene, divinyltoluene, divinylxylene, and divinylnaphthalene. It should be noted that herein, the term "(meth)acrylate" means "acrylate" or "methacrylate", and the term "(meth)acrylic" means "acrylic" or "methacrylic".

Examples of the monomer having a reactive functional group include glycidyl (meth)acrylate and isocyanatoethyl (meth)acrylate.

The hydrophobic non-cross-linkable monomer is not particularly limited as long as the monomer is a non-cross-linkable polymerizable organic monomer having the nature of hydrophobicity, and examples thereof include: (meth)acrylic acid esters such as methyl (meth)acrylate, ethyl (meth)acrylate, butyl (meth)acrylate, and t-butyl (meth)acrylate; and styrene-based monomers such as styrene and methylstyrene.

When the hydrophobic cross-linked polymer is one obtained by copolymerizing the hydrophobic cross-linkable monomer and the monomer having a reactive functional group, the content of a segment derived from the hydrophobic cross-linkable monomer in the hydrophobic cross-linked polymer has a preferred lower limit of 10 wt %, a more preferred lower limit of 20 wt %.

It is preferred that the packing material for ion-exchange chromatography of the present invention has, on the surface of each of the base particles, a polymer layer having a strong cationic group and a weak cationic group. In addition, in the polymer having a strong cationic group and a weak cationic group, the strong cationic group and the weak cationic group are preferably derived from respectively independent monomers. Specifically, it is suitable that the packing material for ion-exchange chromatography of the present invention have a weak cationic group introduced to the surface of each of coated polymer particles formed of: the hydrophobic cross-linked polymer particles; and a layer of a hydrophilic polymer having a strong cationic group copolymerized to the surface of each of the hydrophobic cross-linked polymer particles.

The hydrophilic polymer having a strong cationic group is formed from a hydrophilic monomer having a strong cationic group, and only needs to contain a segment derived from hydrophilic monomers having one or more kinds of strong cationic groups. That is, as a method of producing the hydrophilic polymer having a strong cationic group, there are given: a method involving polymerizing a hydrophilic monomer having a strong cationic group alone; a method involving copolymerizing two or more kinds of hydrophilic monomers each having a strong cationic group; a method involving copolymerizing a hydrophilic monomer having a strong cationic group and a hydrophilic monomer having no strong cationic group; and the like.

The hydrophilic monomer having a strong cationic group is preferably one having a quaternary ammonium group. Specific examples thereof include methacryloyloxyethyltriethylammonium chloride, methacryloyloxyethyldimethylethylammonium chloride, methacryloyloxyethyldimethylbenzylammonium chloride, acryloyloxyethyldimethylbenzylammonium chloride, acryloyloxyethyltriethylammonium chloride, acryloyloxyethyldimethylethylammonium chloride, acrylamidoethyltrimethylammonium chloride, acrylamidoethyltriethylammonium chloride, and acrylamidoethyldimethylethylammonium chloride.

As a method of introducing the weak cationic group to the surface of each of the coated polymer particles, a known method may be used. Specifically, for example, as a method of introducing a tertiary amino group as the weak cationic group, there are given: a method involving copolymerizing the hydrophilic monomer having a strong cationic group on the surface of each of hydrophobic cross-linked polymer particles formed of a hydrophobic cross-linked polymer having a segment derived from a monomer having a glycidyl group, and then allowing a reagent having a tertiary amino group to react with the glycidyl group; a method involving copolymerizing the hydrophilic monomer having a strong cationic group on the surface of each of hydrophobic cross-linked polymer particles formed of a hydrophobic cross-linked polymer having a segment derived from a monomer having an isocyanate group, and then allowing a reagent having a tertiary amino group to react with the isocyanate group; a method involving copolymerizing the hydrophilic monomer having a strong cationic group and a monomer having a tertiary amino group on the surface of each of the hydrophobic cross-linked polymer particles; a method involving using a silane coupling agent having a tertiary amino group to introduce a tertiary amino group to the surface of each of coated polymer particles having a layer of the hydrophilic polymer having a strong cationic group; a method involving copolymerizing the hydrophilic monomer having a strong cationic group on the surface of each of hydrophobic cross-linked polymer particles formed of a hydrophobic cross-linked polymer having a segment derived from a monomer having a carboxy group, and then condensing the carboxy group and a reagent having a tertiary amino group through the use of a carbodiimide; a method involving copolymerizing the hydrophilic monomer having a strong cationic group on the surface of each of hydrophobic cross-linked polymer particles formed of a hydrophobic cross-linked polymer having a segment derived from a monomer having an ester bond, hydrolyzing the ester bond moiety, and then condensing a carboxy group generated by the hydrolysis and a reagent having a tertiary amino group through the use of a carbodiimide; and the like. Of those, a method involving copolymerizing the hydrophilic monomer having a strong cationic group on the surface of each of hydrophobic cross-linked polymer particles formed of a hydrophobic cross-linked polymer having a segment derived from a monomer having a glycidyl group, and then allowing a reagent having a tertiary amino group to react with the glycidyl group, or a method involving copolymerizing the hydrophilic monomer having a strong cationic group on the surface of each of hydrophobic cross-linked polymer particles formed of a hydrophobic cross-linked polymer having a segment derived from a monomer having an isocyanate group, and then allowing a reagent having a tertiary amino group to react with the isocyanate group is preferred.

The reagent having a tertiary amino group to be allowed to react with the reactive functional group such as the glycidyl group or the isocyanate group is not particularly limited as long as the reagent has a tertiary amino group and a functional group capable of reacting with the reactive functional group. Examples of the tertiary amino group and the functional group capable of reacting with the reactive functional group include a primary amino group and a hydroxy group. Of those, a group having a primary amino group at an end is preferred. Specific examples of the reagent having the functional group include N,N-dimethylaminomethylamine, N,N-dimethylaminoethylamine, N,N-dimethylaminopropylamine, N,N-dimethylaminobutylamine, N,N-diethylaminoethylamine, N,N-diethylaminopropylethylamine, N,N-diethylaminobutylamine, N,N-diethylaminopentylamine, N,N-diethylaminohexylamine, N,N-dipropylaminobutylamine, and N,N-dibutylaminopropylamine.

A relative positional relationship between the strong cationic group, preferably a quaternary ammonium salt, and the weak cationic group, preferably a tertiary amino group, is preferably such that the strong cationic group is positioned more distant from the surface of the base particle than the weak cationic group is, in other words, positioned on an outer side. For example, it is preferred that the weak cationic group be present within 30 Å of the surface of the base particle, and the strong cationic group be present within 300 Å of the surface of the base particle and on an outer side with respect to the weak cationic group.

The average particle diameter of the base particles to be used for the packing material for ion-exchange chromatography of the present invention is not particularly limited, but has a preferred lower limit of 0.1 µm and a preferred upper limit of 20 µm. When the average particle diameter is less than 0.1 µm, the pressure in the column may become so high as to cause separation failure. When the average particle diameter is more than 20 µm, the dead volume in the column may become so large as to cause separation failure. It should be noted that herein, the average particle diameter refers to a volume-average particle diameter, and may be measured using a particle size distribution measuring instrument (such as AccuSizer 780/manufactured by Particle Sizing Systems).

Known conditions may be used for the composition of an eluent to be used in the ion-exchange chromatography to be performed in the present invention.

As a buffer to be used for the eluent, a known salt compound-containing buffer or organic solvent is preferably used, and specific examples thereof include Tris-hydrochloride buffer, TE buffer formed of Tris and EDTA, and TBA buffer formed of Tris, borate, and EDTA.

The pH of the eluent is not particularly limited, but has a preferred lower limit of 5 and a preferred upper limit of 10. It is considered that when the pH is set to fall within this range, the weak cationic group also functions effectively as an ion-exchange group (anion-exchange group). The pH of the eluent has a more preferred lower limit of 6 and a more preferred upper limit of 9.

As a salt contained in the eluent, for example, there may be used: a salt formed of a halide and an alkali metal such as sodium chloride, potassium chloride, sodium bromide, or potassium bromide; a salt formed of a halide and an alkaline earth metal such as calcium chloride, calcium bromide, magnesium chloride, or magnesium bromide; or an inorganic acid salt such as sodium perchlorate, potassium perchlorate, sodium sulfate, potassium sulfate, ammonium sulfate, sodium nitrate, or potassium nitrate. In addition, there may be used an organic acid salt such as sodium acetate, potassium acetate, sodiumsuccinate, orpotassiumsuccinate. Any one of the above-mentioned salts may be used alone, or two or more thereof may be used in combination.

The salt concentration of the eluent only needs to be appropriately adjusted depending on assay conditions, but has a preferred lower limit of 10 mmol/L and a preferred upper limit of 2,000 mmol/L, and has a more preferred lower limit of 100 mmol/L and a more preferred upper limit of 1,500 mmol/L.

Further, the eluent to be used in the ion-exchange chromatography of the present invention may contain an antichaotropic ion in order to further enhance separation performance. The antichaotropic ion has the opposite nature to that of a chaotropic ion and has a function of stabilizing a hydration structure. Accordingly, the antichaotropic ion has an augmenting effect on a hydrophobic interaction between the packing material and a nucleic acid molecule. A main interaction in the ion-exchange chromatography of the present invention is an electrostatic interaction, but the separation performance is enhanced when the function of the hydrophobic interaction is further utilized.

Examples of the antichaotropic ion contained in the eluent include a phosphate ion ($PO_4^{3-}$), a sulfate ion ($SO_4^{2-}$), an ammonium ion ($NH_4^+$), a potassium ion ($K^+$), and a sodium ion ($Na^+$). A sulfate ion and an ammonium ion are suitably used among combinations of those ions. Any one of the above-mentioned antichaotropic ions may be used alone, or two or more thereof may be used in combination. It should be noted that some of the above-mentioned antichaotropic ions include components of the salt and buffer contained in the eluent. The case where such component is used is suitable for the present invention because the component has both the nature as the salt contained in the eluent or buffer capacity, and the nature as the antichaotropic ion.

In the eluent for ion-exchange chromatography of the present invention, the concentration of the antichaotropic ion at the time of assay only needs to be appropriately adjusted depending on an object to be assayed, but is desirably 2,000 mmol/L or less in terms of an antichaotropic salt. Specifically, there may be given a method involving gradient elution with the concentration of the antichaotropic salt being in the range of from 0 mmol/L to 2,000 mmol/L. Therefore, the concentration of the antichaotropic salt at the time of the start of the assay does not need to be 0 mmol/L, and the concentration of the antichaotropic salt at the time of the completion of the assay does not need to be 2,000 mmol/L. A method for the gradient elution may be a low-pressure gradient method or may be a high-pressure gradient method, but is preferably a method involving elution while precisely adjusting the concentration based on a high-pressure gradient method.

The antichaotropic ion may be added to only one kind out of eluents to be used in elution, or may be added to a plurality of kinds of eluents. In addition, the antichaotropic ion may have both the following functions: an augmenting effect on the hydrophobic interaction between the packing material and the PCR amplification product or buffer capacity; and an effect of eluting the PCR amplification product from the column.

A column temperature when the PCR amplification product is assayed by the ion-exchange chromatography to be performed in the present invention is preferably 30° C. or more, more preferably 40° C. or more, even more preferably 45° C. or more. When the column temperature in the ion-exchange chromatography is less than 30° C., the hydrophobic interaction between the packing material and the PCR amplification product is weakened, with the result that a desired separation effect is difficult to obtain. Further, as shown in FIGS. 4-1, FIGS. 4-2, FIGS. 5-1, FIGS. 5-2, and Table 3, when the column temperature in the ion-exchange chromatography is less than 45° C., a difference in retention time between a PCR amplification product of methylated DNA treated with the hydrogen sulfite (methylated DNA sample) and a PCR amplification product of unmethylated DNA treated the hydrogen sulfite (unmethylated DNA sample) is small. In addition, when a PCR amplification product of hemimethylated DNA, in which one strand of double-stranded DNA is methylated (the composition of the hemimethylated DNA is similar to that of a mixture of equal amounts of the methylated DNA sample and the unmethylated DNA sample), treated with the hydrogen sulfite (hemimethylated DNA sample) is assayed, the resultant chromatogram is indistinct owing to unsatisfactory separation. On the other hand, when the column temperature is 55° C. or more, a methylated DNA strand-derived PCR amplification product and unmethylated DNA strand-derived PCR amplification product in the hemimethylated DNA sample are separated to be detected as two individual peaks having different retention times, and hence methylation of DNA can be detected even in the hemimethylated DNA sample. Further, when the column temperature is 60° C. or more, the difference in retention time between the methylated DNA sample and the unmethylated DNA sample is further widened and their respective peaks become more distinct as well, and hence the methylation of DNA can be detected more accurately.

Further, an increase in column temperature in the ion-exchange chromatography allows the methylated DNA sample and the unmethylated DNA sample to be distinctly separated, and hence a difference is likely to occur in peak area or peak height between their retention times in accordance with the presence ratio of methylated DNA and unmethylated DNA in the sample DNA. Therefore, an increase in column temperature makes it easier to measure the presence amount or presence ratio of each of methylated DNA and unmethylated DNA in the sample DNA based on the areas or heights of the peaks of the retention times of the methylated DNA sample and the unmethylated DNA sample.

However, a column temperature in the ion-exchange chromatography of 90° C. or more causes double-stranded nucleic acid molecules in the PCR amplification product to dissociate, and hence is not preferred for the assay. Further, a column temperature of 100° C. or more may cause the eluent to boil, and hence is not preferred for the assay. Therefore, it is appropriate that the column temperature when the PCR amplification product is assayed by the ion-exchange chromatography to be performed in the present invention be 30° C. or more and less than 90° C., preferably 40° C. or more and less than 90° C., more preferably 45° C. or more and less than 90° C., more preferably 55° C. or more and less than 90° C., more preferably 55° C. or more and 85° C. or less, even more preferably 60° C. or more and 85° C. or less.

The amount of the sample to be injected into the ion-exchange chromatography column is not particularly limited and only needs to be appropriately adjusted depending on the ion exchange capacity of the column and a sample concentration. A flow rate is preferably from 0.1 mL/min to 3.0 mL/min, more preferably from 0.5 mL/min to 1.5 mL/min. A low flow rate can be expected to improve separation, but an excessively low flow rate may cause the assay to require a long period of time, or may cause a reduction in separation performance due to peak broadening. In contrast, a high flow rate has an advantage in shortening an assay time, but causes a reduction in separation performance due to peak compression. Accordingly, although being a parameter to be appropriately adjusted depending on the performance of the column, the flow rate is desirably set to fall within the above-mentioned range. The retention time of each sample may be determined in advance by subjecting each sample to a preliminary experiment. As a liquid delivery method, a known liquid delivery method such as a linear gradient elution method or a stepwise elution method may be used, but the liquid delivery method in the present invention is preferably a linear gradient elution method. Regarding how large the gradient (slope) is, the eluent to be used in elution only needs to be appropriately adjusted within the range of from 0% to 100% depending on the separation performance of the column and properties of the object to be assayed (in this case, the PCR amplification product).

In the present invention, by subjecting the PCR amplification product of the DNA treated with the hydrogen sulfite to ion-exchange chromatography by the above-mentioned procedure, methylation of DNA in the sample DNA is detected. Herein, to "detect methylation" of DNA means: to measure the presence or absence, or presence amount, of methylated DNA in the DNA; to measure the ratio between the presence amounts of methylated DNA and unmethylated DNA in the DNA; or to measure the proportion of methylation (sometimes referred to as methylation ratio) of the DNA.

More specifically, when the PCR amplification product of the sample DNA treated with the hydrogen sulfite is subjected to ion-exchange chromatography, there is obtained a chromatogram in which different signals are shown depending on the base sequence of DNA contained in the amplification product. By comparing the resultant detection signal from the PCR amplification product of the sample DNA treated with the hydrogen sulfite to: a detection signal from a PCR amplification product of DNA treated with the hydrogen sulfite, the DNA being identical in nucleotide sequence to the sample DNA but being free of methylation (hereinafter referred to as negative control); or a detection signal from a PCR amplification product of DNA treated with the hydrogen sulfite, the DNA being identical in nucleotide sequence to the sample DNA and having a predetermined proportion of methylation (for example, 100%) (hereinafter referred to as positive control), the presence or absence of methylated DNA in the sample DNA can be measured (see FIG. 1 to FIG. 3).

Alternatively, by comparing the detection signal from the PCR amplification product of the sample DNA treated with the hydrogen sulfite to the detection signals from the PCR amplification products of the negative control and the positive control, the presence amount, and ratio of the presence amount to that of unmethylated DNA, of methylated DNA in the sample DNA can be measured. Still alternatively, by comparing detection signals from a plurality of PCR amplification products derived from a plurality of DNAs each treated with the hydrogen sulfite, each of the plurality of DNAs being identical in base sequence to the sample DNA and having a predetermined proportion of methylation (hereinafter referred to as standards) to the detection signal from the PCR amplification product of the sample DNA treated with the hydrogen sulfite, the methylation ratio, presence amount, and ratio of the presence amount to that of unmethylated DNA, of methylated DNA in the sample DNA can be measured (see FIG. 6, FIGS. 7-1, and FIG. 7-2).

In the method of the present invention, DNA having the same nucleotide sequence as the negative control, the positive control, or the standards and synthesized by a chemical approach or a genetic engineering approach may be used in place of the PCR amplification product of the negative control, the positive control, or the standards. Further, in the method of the present invention, a commercially available product may be used in the preparation of the negative control, the positive control, or the standards, and for example, EpiTect Control DNA and Control DNA Set (manufactured by Qiagen) may be used.

In addition, according to the present invention, DNA methylation can be detected also for hemimethylated DNA, in which one strand of double-stranded DNA is methylated. A PCR amplification product of hemimethylated DNA treated with the hydrogen sulfite is a mixture of: a PCR amplification product of methylated DNA treated with the hydrogen sulfite; and a PCR amplification product of unmethylated DNA treated with the hydrogen sulfite. In the ion-exchange chromatography to be performed in the present invention, the methylated DNA strand and the unmethylated DNA strand can be measured in an accurately separate manner, and hence hemimethylated DNA can be detected (see FIGS. 4-1, FIGS. 4-2, FIGS. 5-1, and FIGS. 5-2).

In a preferred embodiment, in the ion-exchange chromatography to be performed in the present invention, a sample containing the PCR amplification product of the sample DNA treated with the hydrogen sulfite, and a sample containing the PCR amplification product of the negative control or the positive control, or the standards are individually subjected to ion-exchange chromatographic assay. When a sample adsorbed on the column is subjected to gradient elution using a plurality of eluents, the PCR amplification product of the sample DNA treated with the hydrogen sulfite and PCR amplification product of the negative control or the positive control, or the standards can be eluted at different retention times depending on their DNA methylation ratios.

A detection signal from the negative control may be acquired by performing hydrogen sulfite treatment and PCR by the above-mentioned procedures using, in place of the sample DNA, DNA that is identical in nucleotide sequence to the sample DNA but is free of methylation, and subjecting the resultant PCR amplification product to ion-exchange chromatography. A detection signal from the positive control may be acquired by performing hydrogen sulfite treatment and PCR by the above-mentioned procedures using, in place of the sample DNA, DNA that is identical in nucleotide sequence to the sample DNA and has a known methylation ratio (for example, 1000), and subjecting the resultant PCR amplification product to ion-exchange chromatography. Alternatively, the detection signal from the negative or positive control may be obtained by subjecting the above-mentioned synthetic DNA or commercially available DNA as the negative or positive control to ion-exchange chromatography.

The detection signals from the standards may be acquired by performing hydrogen sulfite treatment and PCR by the above-mentioned procedures using, in place of the sample DNA, a plurality of DNAs each of which is identical in nucleotide sequence to the sample DNA and has a predetermined proportion of methylation, and subjecting each of the resultant plurality of PCR amplification products to ion-exchange chromatography. Further, a calibration curve may be created from the resultant respective detection signals. Alternatively, the detection signals from the standards may be obtained by subjecting the above-mentioned synthetic DNAs or commercially available DNAs as the standards to ion-exchange chromatography.

Next, the detection signal from the PCR amplification product of the sample DNA treated with the hydrogen sulfite obtained in the chromatography is compared to the detection signal from the negative or positive control, or the standards. The methylation of the sample DNA can be detected based on the difference between both detection signals.

For example, when the retention time of the peak of the detection signal obtained from the PCR amplification product of the sample DNA treated with the hydrogen sulfite is shifted from the retention time of the peak of the negative control, the sample DNA can be determined to be methylated. Further, in this case, as the shift in retention time becomes larger, the methylation ratio can be estimated to be larger. Conversely, the more the retention time of the peak of the detection signal obtained from the PCR amplification product of the sample DNA treated with the hydrogen sulfite is shifted from the retention time of the peak of the 100% methylated positive control to a larger extent, the more the methylation ratio of the sample DNA can be estimated to be smaller. Alternatively, a calibration curve may be created based on the retention times of a plurality of peaks obtained from standards having known methylation ratios, and the methylation ratio of the sample DNA can be determined based on the calibration curve (see FIGS. 7-1 and FIG. 7-2).

Figure 6:
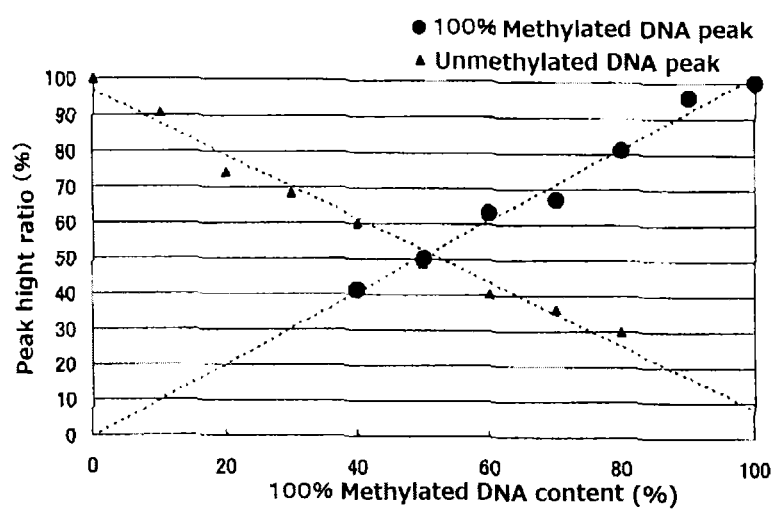
FIG. 6 is a plot of the peak height ratios of PCR amplification products versus the content of 100% methylated DNA in sample DNA.

In addition, for example, by comparing the peak height or peak area of the detection signal obtained from the PCR amplification product of the sample DNA treated with the hydrogen sulfite to the peak height or peak area of the detection signal obtained from the PCR amplification product of DNA treated with the hydrogen sulfite, the DNA having a known methylation ratio and mixing ratio of methylated DNA, the presence ratio of methylated DNA in the sample DNA (for example, presence ratio of unmethylated DNA, or presence ratio of DNA that is methylated at a certain proportion) can be determined (see FIG. 6).

In the method of the present invention, as a method of determining the presence or absence of the peak of the detection signal from the chromatography, there is given peak detection involving using existing data processing software such as LC solution (Shimadzu Corporation), GRAMS/AI (Thermo Fisher Scientific Inc.), or Igor Pro (WaveMetrics, Inc.). A method of determining the presence or absence of the peak involving using LC solution is now exemplified. Specifically, first, a retention time interval in which peaks are to be detected is designated. Next, various parameters are set to remove an unwanted peak such as a noise. Examples thereof include: setting the parameter "WIDTH" larger than the full width at half maximum of an unwanted peak; setting the parameter "SLOPE" larger than the leading slope of an unwanted peak; and choosing whether a low-resolution peak is subjected to vertical partitioning or baseline partitioning by changing the setting of the parameter "DRIFT". Values for the parameters only need to be set to appropriate values depending on the chromatogram because the chromatogram to be obtained varies depending on, for example, assay conditions, the kind of a selected genetic marker, and the amount of a specimen.

According to the method of detecting methylated DNA of the present invention, methylated DNA can be detected rapidly, simply, and highly accurately. An example of the application of the method of detecting methylated DNA of the present invention may be application to a clinical examination. The methylation status of DNA is known to affect the canceration of cells. In particular, there are many reports that aberrant DNA methylation of a CpG island is involved in carcinogenesis (see, for example, JP-A-2010-063413). Therefore, the method of detecting methylated DNA of the present invention can be suitably applied to a clinical examination such as a cancer development examination or a cancer development risk examination.

Further, in the method of the present invention, differential data may be obtained by subtracting the detection signal obtained from the negative control from the detection signal obtained from the PCR amplification product of the sample DNA treated with the hydrogen sulfite. When the differential data is obtained, the signal from unmethylated DNA (noise) can be removed from the detection signal of the sample DNA as a whole to extract only the signal from methylated DNA. The differential data corresponds to the detection signal derived from methylated DNA in the sample DNA. For example, when the peak of a retention time different from that of the negative control can be detected in the differential data, the sample DNA may be considered to contain methylated DNA. Further, by comparing the peak retention time, peak height, or peak area of the differential data to that of the detection signal obtained from the negative control, the positive control, or the standards, the methylation ratio or presence ratio of methylated DNA in the sample DNA can be determined. By using the differential data, methylated DNA can be detected or analyzed even in a sample from which a methylated DNA-derived signal component is detected only faintly, such as: sample DNA having a low presence ratio of methylated DNA; or sample DNA containing methylated DNA having a low methylation ratio. Therefore, the use of the differential data allows more highly accurate analysis of methylated DNA in the sample DNA. It should be noted that when the differential data is obtained, the DNA amounts of the sample DNA and DNA to be used as the negative control are preferably equal. The DNA amounts may be confirmed by a measurement method such as absorbance measurement.

The differential data is more effective in a clinical examination such as a cancer development examination or a cancer development risk examination. A specimen to be harvested for the clinical examination as described above may contain normal cells, or may contain a large number of cells in a precancerous state in which DNA methylation has not progressed to a significant extent. By using the differential data, the influence of unmethylated DNA derived from normal cells in the specimen or normal DNA in precancerous cells can be removed. Consequently, methylated DNA can be detected more highly accurately, and moreover, the cancer development or cancer development risk assessment can be performed more accurately through the utilization of the result of the detection.

Another example of the application of the method of detecting methylated DNA of the present invention may be application to analysis of the differentiation state of cells. It is known that a methylation pattern on a genome serves as a determinant of cell differentiation. Undifferentiated stem cells (such as ES cells, iPS cells, and various adult stem cells) and differentiated cells have different methylation patterns of DNA in the respective cells. The use of the method of detecting methylated DNA of the present invention allows analysis of a difference in methylation pattern depending on the differentiation state of cells, and hence allows sophisticated analysis of a differentiation state of cells such as the differentiation stage of cells used in DNA extraction or whether or not cells in different differentiation states are mixed.

As described above, methylated DNA can be separated or detected by using the above-mentioned column and eluent for ion-exchange chromatography. Therefore, the present invention provides a column for ion-exchange chromatography to be used for the detection of methylated DNA, which is packed with the above-mentioned column packing material containing the base particles each having both a strong cationic group and a weak cationic group on the surface, and also provides an eluent for ion-exchange chromatography to be used for the detection of methylated DNA, containing the antichaotropic ion described above. The column or eluent of the present invention, when provided to the public or when its provision to the public is announced, may be distinguished from other columns or eluents by having a tag or label stating that the column or eluent may be used for the detection of methylated DNA, or by being described on paper or an electronic medium (such as an instruction manual, a catalog, a pamphlet, a CD, or the Web) that describes that the column or eluent is used for the detection of methylated DNA.

Further, the column of the present invention described above may also be provided as a kit, for the detection of methylated DNA, in combination with one or more of: devices and members to be used in ion-exchange chromatography (such as a pump, a gradient mixer, and a guard column); reagents to be used in ion-exchange chromatography (such as the eluent of the present invention, and a column washing solution); and members and reagents to be used in the respective steps of the detection method of the present invention (such as a column and reagent for DNA extraction and a reagent to be used in the PCR amplification step (such as a primer and a polymerase)). As in the case of the column of the present invention or the eluent of the present invention, the kit of the present invention, when provided to the public or when its provision to the public is announced, may be distinguished from other columns and eluents by having a tag or label stating that the kit may be used for the detection of methylated DNA, or by being described on paper or an electronic medium (such as an instruction manual, a catalog, a pamphlet, a CD, or the Web) that describes that the kit is used for the detection of methylated DNA.

EXAMPLES

The present invention is described below in detail by way of Examples, but the present invention is not limited to the following Examples.

[Reference Example 1] Preparation of Anion Exchange Column

To 2,000 mL of a 3 wt % polyvinyl alcohol (manufactured by The Nippon Synthetic Chemical Industry Co., Ltd.) aqueous solution in a reaction vessel with a stirrer, a mixture of 200 g of tetraethylene glycol dimethacrylate (manufactured by Shin-Nakamura Chemical Co., Ltd.), 100 g of triethylene glycol dimethacrylate (manufactured by Shin-Nakamura Chemical Co., Ltd.), 100 g of glycidyl methacrylate (manufactured by Wako Pure Chemical Industries, Ltd.), and 1.0 g of benzoyl peroxide (manufactured by Kishida Chemical Co., Ltd.) was added. The stirred mixture was heated to be polymerized under a nitrogen atmosphere at 80° C. for 1 hour. Next, 100 g of methacryloyloxyethyltrimethylammonium chloride (manufactured by Wako Pure Chemical Industries, Ltd.) as a hydrophilic monomer having a strong cationic group was dissolved in ion-exchanged water. The solution was added to the same reaction vessel, and the stirred contents were similarly polymerized under a nitrogen atmosphere at 80° C. for 2 hours. The resultant polymerized composition was washed with water and acetone to obtain coated polymer particles each having a layer of a hydrophilic polymer having a quaternary ammonium group on the surface. The obtained coated polymer particles were subjected to measurement using a particle size distribution measuring instrument (AccuSizer 780/manufactured by Particle Sizing Systems) and found to have an average particle diameter of 10 μm.

10 g of the obtained coated polymer particles was dispersed in 100 mL of ion-exchanged water to prepare a slurry before reaction. Next, to the stirred slurry, 10 mL of N,N-dimethylaminopropylamine (manufactured by Wako Pure Chemical Industries, Ltd.) was added to perform a reaction at 70° C. for 4 hours. After the completion of the reaction, the supernatant was removed using a centrifuge (manufactured by Hitachi, Ltd., "Himac CR20G"), followed by washing with ion-exchanged water. After the washing, the supernatant was removed using a centrifuge. The washing with ion-exchanged water was repeated an additional 4 times to obtain a packing material for ion-exchange chromatography having a quaternary ammonium group and a tertiary amino group on the surface of each of the base particles.

The packing material for ion-exchange chromatography was packed into a stainless-steel column (column size: 4.6 mm in inner diameter×20 mm in length) of a liquid chromatography system.

[Reference Example 2] Preparation of Specimen Cells

1) Culture of LoVo, LS174T, and HCT116 Cells

In order to obtain 100% methylated DNA, unmethylated DNA, and heteroduplex DNA thereof (hemimethylated DNA) of a CDKN2A gene promoter site (SEQ ID NO: 1), three kinds of cell lines LoVo, LS174T, and HCT116 having the promoter gene in the respective statuses were purchased (manufactured by DS Pharma Biochemical). Culture was performed under medium conditions suited for each type of cells. LoVo was cultured in Ham's F-12 (F-12 Nutrient Mixture) medium supplemented with 10% fetal bovine serum (FBS) in a humidified chamber in the presence of 5% $CO_2$ at 37° C. (B. Drewinko, M. M. Romsdahl, L. Y. Yang., Cancer Res. 36, 1976, 467). LS174T was cultured in minimum essential medium (MEM) Earle's medium supplemented with 10% FBS and 1% non-essential amino acids (NEAA) in a humidified chamber in the presence of 5% $CO_2$ at 37° C. (B. H. Tom, L. P. Rutzky, M. M. Jakstys. In Vitro. 12, 1976, 180). HCT116 was cultured in McCoy's 5A medium supplemented with 10% FBS in a humidified chamber in the presence of 5% $CO_2$ at 37° C. (M. G. Brattain, W. D. Fine, J. Thompson. Cancer Res. 41, 1981, 1751). The culture was performed using a 75-mL cell culture flask, and the cells after the completion of the culture were collected, pelleted, and stored at −80° C. by conventional methods.

2) Culture of DHL-9 and 293T Cells

In order to obtain methylated DNA and unmethylated DNA of a MTAP gene promoter site (SEQ ID NO: 5), two kinds of cell lines DHL-9 and 293T having the promoter gene in the respective statuses were used. Culture was performed under medium conditions suited for each type of cells. DHL-9 was cultured in Roswell Park Memorial Institute Tissue Culture Medium 1640 medium supplemented with 10% (v/v) FBS and 100 U/mL penicillin, 100 µg/mL streptomycin and 2 mmol/L L-glutamine in a humidified chamber in the presence of 5% $CO_2$ at 37° C. 293T was cultured in Dulbecco's modified Eagle's medium (DMEM) medium supplemented with 10% (v/v) FBS and 100 U/mL penicillin and 100 µg/mL streptomycin in a humidified chamber in the presence of 5% $CO_2$ at 37° C. The culture was performed using a 75-mL cell culture flask, and the cells after the completion of the culture were collected, pelleted, and stored at −80° C. by conventional methods.

[Example 1] Detection of Methylated DNA from Specimen Cells

1) Extraction and Hydrogen Sulfite Treatment of Genomic DNA

Genomic DNA of the cell line LoVo, LS174T, HCT116, DHL-9, or 293T cultured in Reference Example 2 was extracted from the cell pellets stored at −80° C. using QIAamp DNA Mini Kit (50) (manufactured by Qiagen) and was measured for a DNA concentration with a spectrophotometer, and then stored at −80° C. until use. 1 µg of each genomic DNA was prepared and treated with a hydrogen sulfite using EpiTect Bisulfite Kit (48) (manufactured by Qiagen), followed by purification. The DNA after the hydrogen sulfite treatment was used in the subsequent operation on the assumption that the whole was collected at the time of the purification (20 ng/µL). In addition, DNA not treated with the hydrogen sulfite was adjusted to 10 ng/µL and used in the subsequent operation. The prepared DNA was stored at −20° C. until use.

2) PCR

The hydrogen sulfite-treated genomic DNA obtained in the section 1) was amplified by PCR. The PCR was performed in 25 µL of a reaction solution containing 10 ng of template DNA, GeneAmp 1×PCR buffer (manufactured by Life Technologies), 200 µmol/L GeneAmp dNTP Mix (manufactured by Life Technologies), 0.75 U AmpliTaq Gold DNA Polymerase (manufactured by Life Technologies), and 0.25 µmol/L forward and reverse primers. In the PCR, initial heat denaturation was performed at 94° C. for 10 minutes, then 94° C. for 30 seconds→57° C. (when using F3-R3 primers) for 30 seconds or 58° C. (when using F4-R3 primers) for 30 seconds→72° C. for 30 seconds was defined as 1 cycle and 40 cycles were continuously performed, and further, an extension reaction was performed at 72° C. for 7 minutes. After the completion of the PCR, 5 µL of the reaction solution was mixed with 1 µl of a loading dye solution and then the mixture was applied to 3% agarose gel supplemented in advance with ethidium bromide and electrophoresed, and the PCR amplification product was observed to confirm that a PCR amplification product of interest was obtained.

3) HPLC Assay

The anion exchange column prepared in Reference Example 1 was used to perform ion-exchange chromatography under the following conditions to separately detect the respective PCR amplification products obtained in the section 2).

System: LC-20A series (manufactured by Shimadzu Corporation)

Eluent: eluent A: 25 mmol/L Tris-hydrochloride buffer (pH 7.5)

eluent B: 25 mmol/L Tris-hydrochloride buffer (pH 7.5)+1 mol/L ammonium sulfate

Assay time: An assay time was 10 min.

Elution method: The mixing ratio of the eluent B was linearly increased under the following gradient condition: 0 min (eluent B: 40%)→10 min (eluent B: 100%).

| Specimen: | |
|---|---|
| LoVo (methylated DNA) PCR amplification product | 136 bp |
| LS174T (unmethylated DNA) PCR amplification product | 136 bp |
| HCT116 (hemimethylated DNA) PCR amplification product | 136 bp |
| LoVo (methylated DNA) PCR amplification product | 77 bp |
| LS174T (unmethylated DNA) PCR amplification product | 77 bp |
| HCT116 (hemimethylated DNA) PCR amplification product | 77 bp |
| DHL-9 (methylated DNA) PCR amplification product | 202 bp |
| 293T (unmethylated DNA) PCR amplification product | 202 bp |

Flow rate: 1.0 mL/min

Detection wavelength: 260 nm

Sample injection amount: 5 µL (sample derived from LoVo, LS174T, or HCT116)

7 µL (sample derived from DHL-9 or 293T)

Column temperature: 40° C. to 85° C.

A peak resolution Rs between the PCR amplification product of methylated DNA and the PCR amplification product of unmethylated DNA is represented by the following equation, where the retention times of the respective peaks are defined as $t_{R1}$ and $t_{R2}$ ($t_{R1} < t_{R2}$) and the full widths at half maximum of the respective peaks are defined as $W_{0.5h1}$ and $W_{0.5h2}$, in accordance with the definition in the Japanese Pharmacopoeia and General rules for high performance liquid chromatography of JIS.

$$Rs = 1.18 \times \left( \frac{t_{R2} - t_{R1}}{W_{0.5h1} + W_{0.5h2}} \right)$$

It should be noted that the same unit is used for $t_{R1}$, $t_{R2}$, $W_{0.5h1}$, and $W_{0.5h2}$. In addition, regarding a method of calculating the peak full width at half maximum $W_{0.5h}$, the $W_{0.5h}$ is represented by the following equation, where the peak is normally distributed with a standard deviation $\sigma$.

$$W_{0.5h} = 2.354\sigma$$

[Experiment 1] Methylation Analysis of CDKN2A Gene

Promoter Region

Figure 2:
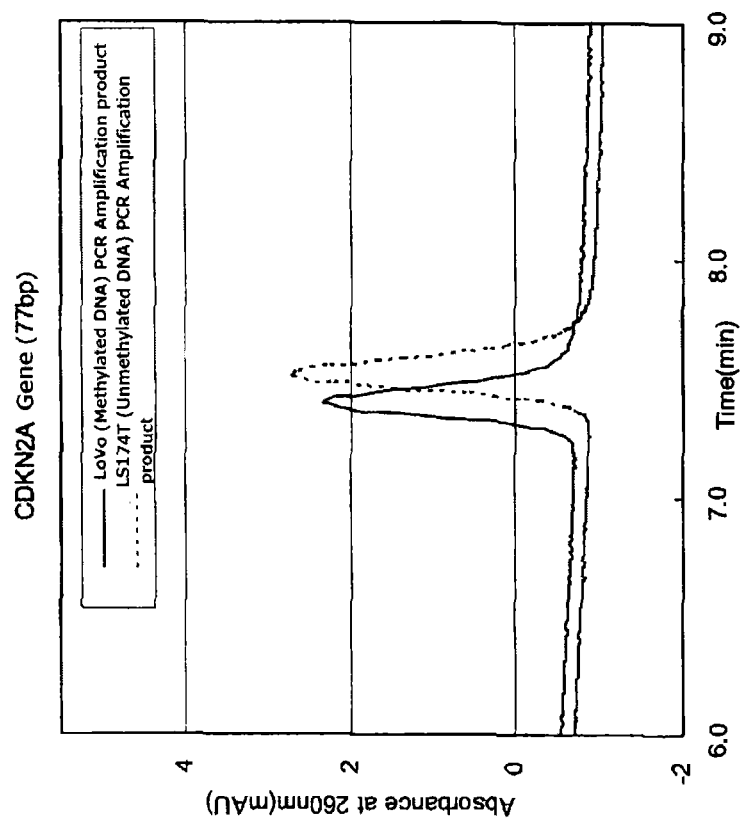
FIG. 2 is a chromatogram of PCR amplification products (77 bp) of methylated DNA and unmethylated DNA derived from a CDKN2A gene promoter, using an anion exchange column obtained in Reference Example 1.

In accordance with the procedure of Example 1, methylation of the CDKN2A gene promoter region in DNAs extracted from LoVo and LS174T was detected. In the PCR, from the CDKN2A gene promoter DNA (SEQ ID NO: 1) of each hydrogen sulfite-treated DNA, a 136-bp region and a 77-bp region were amplified using primers CDKN2A-F3 and CDKN2A-R3 (SEQ ID NOS: 2 and 3), and using primers CDKN2A-F4 and CDKN2A-R3 (SEQ ID NOS: 4 and 3), respectively. The column temperature in the ion-exchange chromatographic assay was set to 40° C. The sequence of the template DNA, the sequences of the primers, the amplification product size, and the number of CpGs in the CpG island in the amplified regions of the sequence of the promoter are shown in Table 1. The results of the ion-exchange chromatographic assay are shown in FIG. 1 and FIG. 2.

TABLE 1

Template: CDKN2A promoter sequence (SEQ ID NO: 1)

```
ggagttaata gcacctcctc cgagcactcg ctcacggcgt cccctttgcct ggaaagatac cgcggtccct ccagaggatt tgagggacag ggtcggaggg ggctcttccg ccagcaccgg aggaagaaag aggaggggct ggctggtcac cagagggtgg ggcggaccgc gtgcgctcgg cggctgcgga gaggggggaga gcaggcagcg ggcggcgggg agcagcatgg agccggcggc ggggagcagc atggagcctt cggctgactg gctggccacg gccgcggccc ggggtcgggt
(the underlines represent primer binding sites,
atg: translation start codon)
```

TABLE 1-continued

| SEQ ID NO: | Primer name | Sequence (5'-3') | PCR amplification product size (bp) | Number of CpGs |
|---|---|---|---|---|
| 2 | CDKN2A-F3 | Tagaggatt tgagggaTag ggt | 136 | 10 |
| 3 | CDKN2A-R3 | tAcctActct ccccctctc | | |
| 4 | CDKN2A-F4 | aggaggggTt ggTtggtTaT Tag | 77 | 7 |
| 5 | CDKN2A-R3 | tAcctActct ccccctctc | | |

T: converted by sodium bisulfite and PCR
A: complementary to T

[Experiment 2] Methylation Analysis of MTAP Gene Promoter Region

Figure 3:
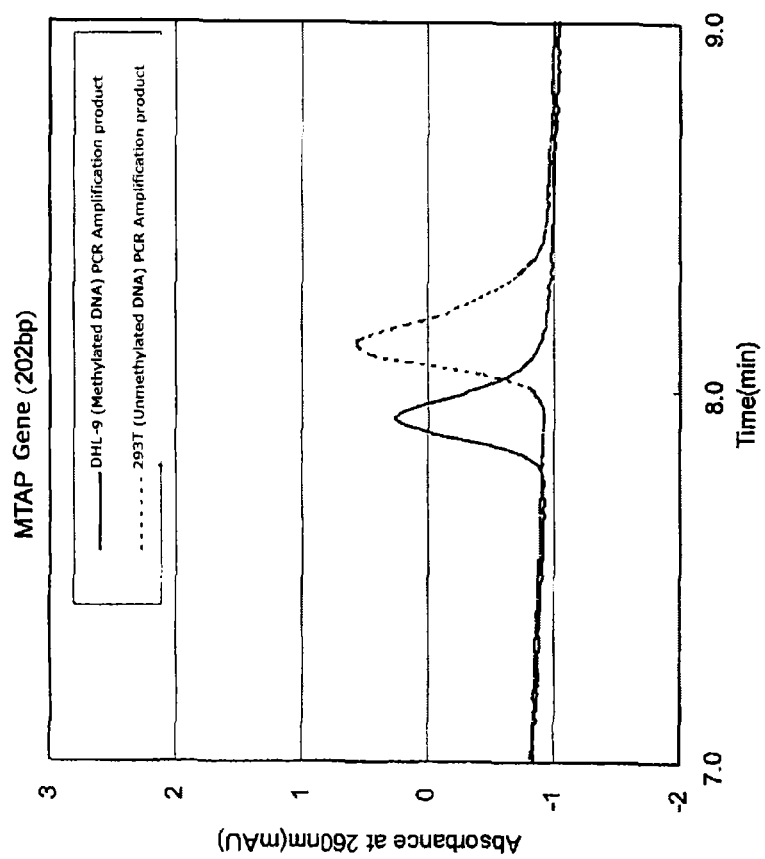
FIG. 3 is a chromatogram of PCR amplification products (202 bp) of methylated DNA and unmethylated DNA derived from a MTAP promoter gene, using an anion exchange column obtained in Reference Example 1.
Figures 1, 5:
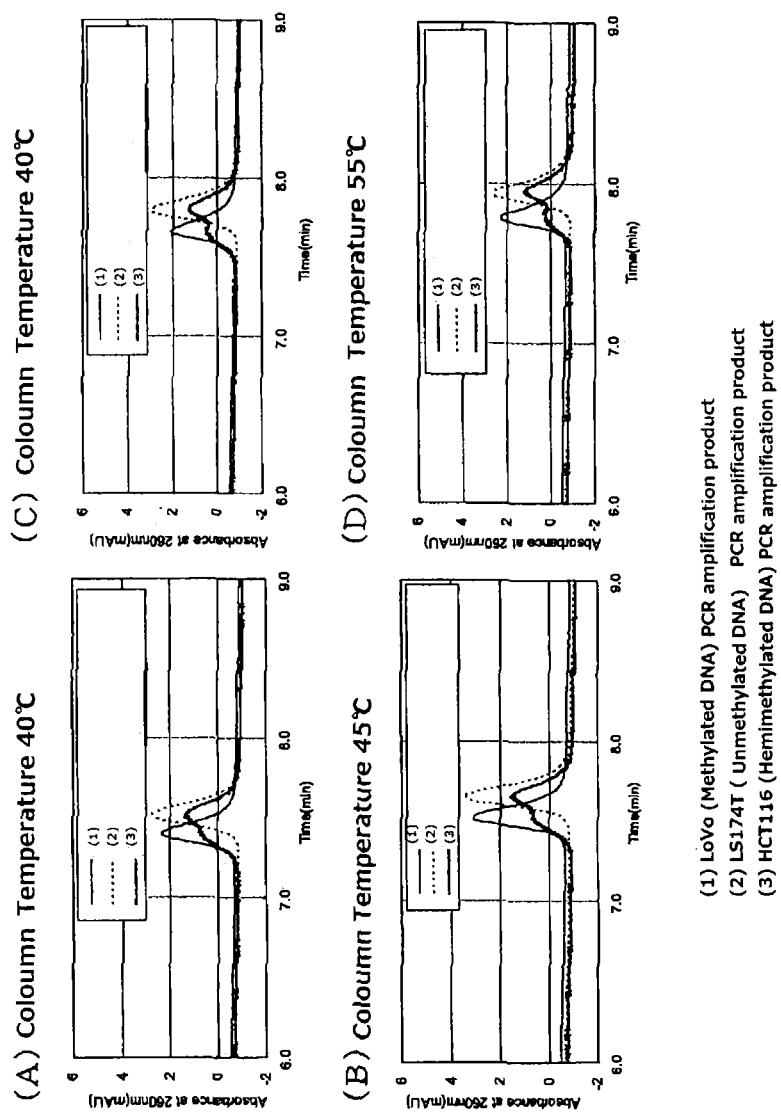
Figures 2, 5:
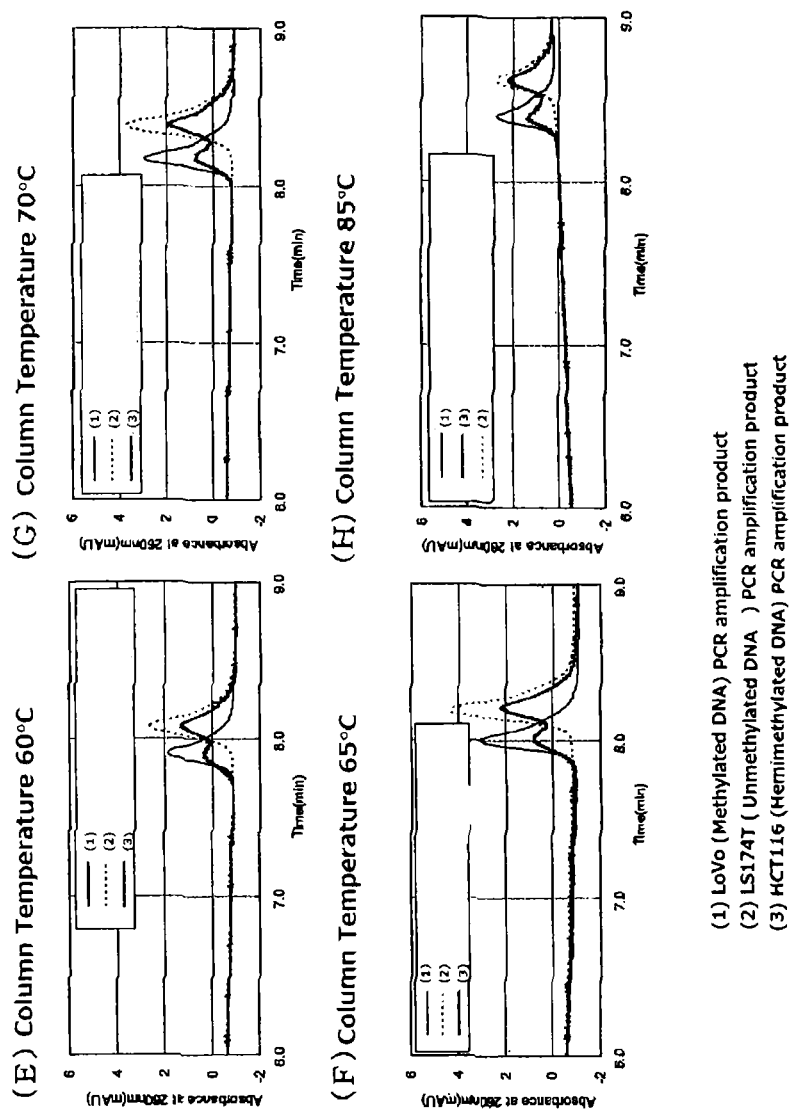

In accordance with the procedure of Example 1, methylation of the MTAP gene promoter region in DNAs extracted from DHL-9 and 293T was detected. In the PCR, a 202-bp region in MTAP gene promoter DNA (SEQ ID NO: 5) of each hydrogen sulfite-treated DNA was amplified using primers (SEQ ID NOS: 6 and 7). The column temperature in the ion-exchange chromatographic assay was set to 70° C. The sequence of the template DNA, the sequences of the primers, the amplification product size, and the number of CpGs in the CpG island in the amplified regions of the sequence of the promoter are shown in Table 2. The results of the ion-exchange chromatographic assay are shown in FIG. 3.

TABLE 2

Template: MTAP promoter sequence (SEQ ID NO: 5)

```
ctgagtcttgggtcaagtccatcccagctctgtcctccaggaatcaagggaaatacgcaaacccgcggtgggttcgcagccgc aggaaggacaaatcttgccccgccgcggcggccgccccgcgttagctgcctaagagaatctccgtggccggccagtacccgc cttggtgaggattctccctcccgcgagaacttctggaatgccgccgggccagattttgcagctgaggcctccgacgccactaat attgggccaagcagggagtgctgctcttccttataaggttttagcgaaagttaagtaagccaattaaagtgcaaaacacaca gtctggaacaatacagcgctctataaatggtctccattattatcattatccgttagttataactggggataaaaaaaaaaaa aaacgacaaaaacctggagaaccggaaaggtctgcaaaaggggcggaacgcgggaacttcgatttggggaaggggtggc gggggagatcccacacaagcagccaatccagctgtcccggggaggaagaggaggagtcaaggcccgcccctggtctccgca ctgctcactcccgcgcagtgaggttggcacagccaccgctctgtggctcgcttggttcccttagtcccgagcgctcgcccactgca gattcctttcccgtgcagacatggcctctggcaccaccaccaccg
```

| SEQ ID NO: | Primer name | Sequence (5'-3') | PCR amplification product size (bp) | Number of CpGs |
|---|---|---|---|---|
| 6 | Forward | GGTGGGTTAGTAGTAGTAGGAAGGA | 202 | 16 |
| 7 | Reverse | CTCCCTACTTAACCCAATATTAAT | | |

The regions in the squares are primer binding sites, atg: translation start codon

[Experiment 3] Methylation Analysis of CDKN2A Gene Promoter Region

In accordance with the procedure of Example 1, methylation of the CDKN2A gene promoter region in DNAs extracted from LoVo, LS174T, and HCT116 was detected. In the PCR, from the CDKN2A gene promoter DNA (SEQ ID NO: 1) of each hydrogen sulfite-treated DNA, a 136-bp region and a 77-bp region were amplified in the same manner as in Experiment 1. The column temperature in the ion-exchange chromatographic assay was set to from 40° C. to 85° C.

In FIGS. 4-1, FIGS. 4-2, FIGS. 5-1, and FIGS. 5-2, the results of the ion-exchange chromatographic assay of the PCR amplification products (136 bp and 77 bp for each) of 100% methylated DNA, unmethylated DNA, and hemimethylated DNA each treated with the hydrogen sulfite, the DNAs being derived from the CDKN2A gene promoter, are shown. The column temperature in the ion-exchange chromatography in FIGS. 4-1, FIGS. 4-2, FIGS. 5-1, and FIGS. 5-2 is 40° C. in (A), 45° C. in (B), 50° C. in (C), 55° C. in (D), 60° C. in (E), 65° C. in (F), 70° C. in (G), and 85° C. in (H). In Table 3, the peak resolution Rs of the PCR amplification product (77 bp) at each column temperature is shown.

TABLE 3

| Column temperature (° C.) | Peak of retention time (sec) | | | Resolution Rs |
|---|---|---|---|---|
| | CDKN2A: 100% methylated ($t_{R1}$) | CDKN2A: hemimethylated | CDKN2A: unmethylated ($t_{R2}$) | |
| 35 | 435.8 | 442.2 | 441.6 | 0.42 |
| 40 | 444.2 | 450.6 | 451.2 | 0.59 |
| 45 | 451.2 | 459.5 | 459.5 | 0.59 |
| 50 | 459.5 | 468.5 | 467.8 | 0.69 |
| 55 | 467.2 | 467.8/477.4 | 476.8 | 0.81 |
| 60 | 474.2 | 474.2/485.1 | 484.5 | 0.86 |
| 65 | 480.0 | 480.6/492.8 | 491.5 | 0.97 |
| 70 | 490.2 | 490.9/503.7 | 503.0 | 1.06 |
| 85 | 504.0 | 504.0/517.4 | 517.4 | 1.08 |

Results and Discussion Through Experiments 1 to 3

From the results of the assay by HPLC (FIG. 1, FIG. 2, and FIG. 3), it was confirmed that methylated DNA and unmethylated DNA were able to be separately detected accurately. In unmethylated DNA, cytosine of the CpG island in the template promoter sequence is converted to uracil by the hydrogen sulfite treatment, and amplified as thymine in PCR. On the other hand, in methylated DNA, methylated cytosine of the CpG island remains as cytosine without being changed by the hydrogen sulfite treatment, and hence is amplified as cytosine in PCR. Accordingly, the results shown in FIG. 1, FIG. 2, and FIG. 3 show that methylated DNA and unmethylated DNA have been separately detected by virtue of the difference between cytosine and thymine of the PCR amplification products. It should be noted that as a result of pyrosequencing analysis, it was confirmed that the DNAs of LoVo and DHL-9 were 100% methylated.

The number of CpG islands in the PCR-amplified region of each template promoter sequence was as follows: 10/136 bp in the sample subjected to the assay of FIG. 1; 7/77 bp in the sample subjected to the assay of FIG. 2; and 16/202 bp in the sample subjected to the assay of FIG. 3. Therefore, such methylation that a base difference of slightly less than 10% occurs in the sequence of the PCR amplification product can be accurately detected by the method of the present invention within a short period of time.

In addition, as shown in FIGS. 4-1, FIGS. 4-2, FIGS. 5-1, FIGS. 5-2, and Table 3, it was confirmed that peak separation in HPLC between the PCR amplification products of methylated DNA and unmethylated DNA each treated with the hydrogen sulfite was improved along with an increase in column temperature. Therefore, through the adjustment of the column temperature in the ion-exchange chromatographic assay in the method of the present invention, methylated DNA and unmethylated DNA can be more accurately detected.

[Experiment 4] Analysis of Methylated/Unmethylated DNA Mixed Sample

1) Preparation of Methylated/Unmethylated DNA Mixed Sample

In accordance with the procedure of Example 1, 100% methylated DNA and unmethylated DNA of the CDKN2A gene promoter site (SEQ ID NO: 1) were prepared and treated with a hydrogen sulfite using EpiTect Bisulfite Kit (48) (manufactured by Qiagen). The 100% methylated DNA and unmethylated DNA each treated with the hydrogen sulfite were mixed at a predetermined proportion to prepare a methylated/unmethylated DNA mixed sample. Each of the DNAs was amplified by PCR by the same procedure of Experiment 1 to obtain a PCR amplification product of 136 bp.

2) HPLC Assay

In accordance with the procedure of Example 1, the PCR amplification products obtained in the foregoing were subjected to ion-exchange chromatography. The column temperature was set to 70° C. Each PCR amplification product was separately detected, and the peak height of the retention time was measured. The ratio of the peak height of 100% methylated DNA in each sample to the peak height of the sample containing only 100% methylated DNA (content of methylated DNA: 100%), and the ratio of the peak height of unmethylated DNA in each sample to the peak height of the sample containing only unmethylated DNA (content of methylated DNA: 0%) were each obtained. FIG. 6 is a graph obtained by plotting the peak height ratio between 100% methylated DNA and unmethylated DNA in each sample DNA versus the content of 100% methylated DNA in the sample DNA.

As shown in FIG. 6, 100% methylated DNA and unmethylated DNA in the sample DNA were separated into distinctly different peaks by HPLC, and moreover, the ratios of their peak heights were proportional to their respective presence ratios in the sample DNA. Therefore, when a peak height in HPLC is measured in the method of the present invention, the presence ratio of DNA having different methylation ratios contained in sample DNA can be measured.

[Experiment 5] Analysis of DNA Samples Having Different Methylation Ratios

Eight synthetic DNAs each having a total length of 384 bp and formed of adenine (A) at 48 bp, thymine (T) at 158 bp, guanine (G) at 100 bp, cytosine at 0 bp, and 39 CpG sites at 78 bp, the DNAs having different methylation ratios, ranging from DNA in which all the 39 CpG sites were methylated (100% methylated DNA) to DNA in which none of the 39 CpG sites were methylated (0% methylated DNA), were synthesized. It should be noted that for 50% methylated DNAs, three patterns of DNAs in which methylation sites were near the 5' side, near the 3' side, and near the central, respectively, were synthesized. The methylation ratio and number of methylated CpGs in the CpG island of each of the synthetic DNAs are shown in Table 4.

TABLE 4

| Synthetic DNA No. | Methylation ratio (sites on CpG island) | Number of methylated CpGs | Number of unmethylated CpGs |
| --- | --- | --- | --- |
| 1 | 100% | 39 | 0 |
| 2 | 0% | 0 | 39 |
| 3 | 25% (random) | 10 | 29 |
| 4 | 50% (random) | 20 | 19 |
| 5 | 75% (random) | 30 | 9 |
| 6 | 50% (near the 5' side) | 20 | 19 |
| 7 | 50% (near the 3' side) | 20 | 19 |
| 8 | 50% (central) | 20 | 19 |

Figure 7:
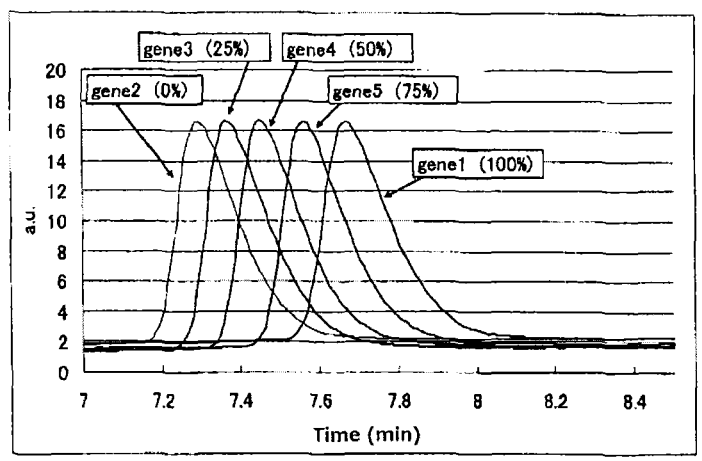
Figure 1:
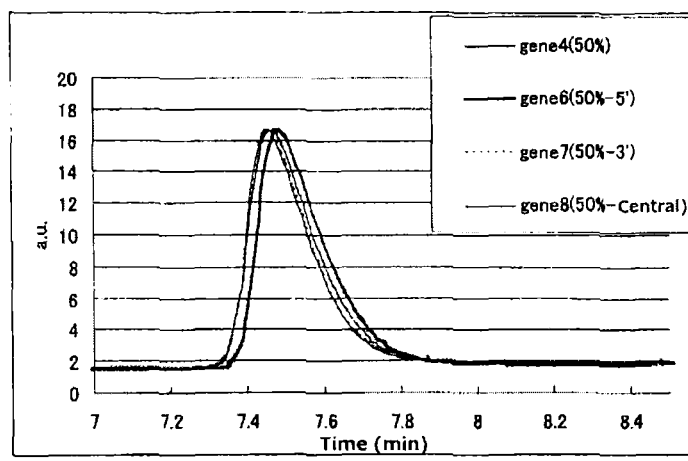
Figures 2, 7:
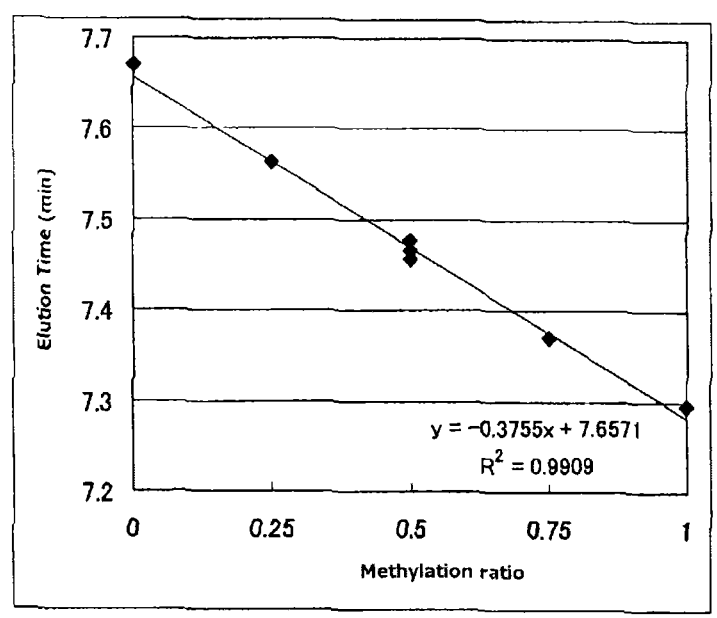

Methylation was detected for the eight synthetic DNAs in accordance with the procedure of Example 1. A HPLC chromatogram of DNAs having different DNA methylation ratios (0%, 25%, 50%, 75%, and 100%) is shown in FIG. 7-1A, a HPLC chromatogram of 50% methylated DNAs having different DNA methylation sites (random, near the 5' side, near the 3' side, and central) is shown in FIG. 7-1B, and plotted data of elution time (retention time) in HPLC versus DNA methylation ratio is shown in FIG. 7-2C. The elution time in the HPLC assay had an extremely high correlation to the DNA methylation ratio. Further, it was confirmed that the 50% methylated DNAs show almost the same retention time irrespective of the methylation sites. This showed that the retention time was determined depending on the methylation ratio irrespective of the methylation sites in DNA. Therefore, when the retention time in HPLC is measured in the method of the present invention, the methylation ratio in the sample DNA can be measured.

The invention claimed is:

1. A method of detecting methylated DNA, comprising (1), (2), and (3):
   (1) treating sample DNA with a hydrogen sulfite;
   (2) amplifying the sample DNA treated with the hydrogen sulfite by PCR; and
   (3) subjecting the resultant PCR amplification product to ion-exchange chromatography.

2. A method of detecting methylated DNA, comprising (1), (2), and (3'):
   (1) treating sample DNA with a hydrogen sulfite;
   (2) amplifying the sample DNA treated with the hydrogen sulfite by PCR; and
   (3') subjecting the resultant PCR amplification product to ion-exchange chromatography at a column temperature of 45° C. or more and less than 90° C.

3. The method according to claim 1, wherein the ion-exchange chromatography comprises anion-exchange chromatography.

4. The method according to claim 1, wherein a column packing material used in the ion-exchange chromatography comprises base particles each having both a strong cationic group and a weak cationic group on a surface thereof on its surface.

5. The method according to claim 1, wherein an eluent used in elution of the PCR amplification product in the ion-exchange chromatography comprises an antichaotropic ion.

6. The method according to claim 5, wherein the antichaotropic ion comprises any one or both of a sulfate ion and an ammonium ion.

7. The method according to claim 1, further comprising comparing a detection signal obtained in the ion-exchange chromatography of the PCR amplification product of the sample DNA treated with the hydrogen sulfite to a detection signal obtained in ion-exchange chromatography of:
- a PCR amplification product of DNA treated with the hydrogen sulfite, the DNA being identical in nucleotide sequence to the sample DNA but being free of methylation; or
- a PCR amplification product of DNA treated with the hydrogen sulfite, the DNA being identical in nucleotide sequence to the sample DNA and having a predetermined proportion of methylation.

8. The method according to claim 7, further comprising measuring, based on results of the comparing step, presence or absence, a methylation ratio, or a presence ratio of methylated DNA in the sample DNA.

9. The method according to claim 1, further comprising subtracting a detection signal obtained in ion-exchange chromatography of a PCR amplification product of DNA treated with the hydrogen sulfite, the DNA being identical in nucleotide sequence to the sample DNA but being free of methylation from a detection signal obtained in the ion-exchange chromatography of the PCR amplification product of the sample DNA treated with the hydrogen sulfite to obtain differential data.

10. The method according to claim 9, further comprising measuring, based on the differential data, presence or absence, a methylation ratio, or a presence ratio of methylated DNA in the sample DNA.

11. A method of extracting a signal of methylated DNA from a signal of sample DNA, the method comprising (1) to (6):
(1) treating sample DNA with a hydrogen sulfite;
(2) amplifying the sample DNA treated with the hydrogen sulfite by PCR;
(3) subjecting a PCR amplification product obtained in (2) to ion-exchange chromatography;
(4) treating DNA that is identical in nucleotide sequence to the sample DNA but is free of methylation with the hydrogen sulfite, followed by PCR amplification;
(5) subjecting a PCR amplification product obtained in (4) to ion-exchange chromatography; and
(6) subtracting a detection signal in chromatography obtained in (5) from a detection signal in chromatography obtained in (3) to obtain differential data.

12. The method according to claim 7, wherein the detection signal is based on a retention time in the ion-exchange chromatography.

13. The method according to claim 9, wherein the detection signal is based on a retention time in the ion-exchange chromatography.

14. The method according to claim 11, wherein the detection signal is based on a retention time in the ion-exchange chromatography.

* * * * *

SEQUENCE LISTING

<160> NUMBER OF SEQ ID NOS: 7

<210> SEQ ID NO 1
<211> LENGTH: 300
<212> TYPE: DNA
<213> ORGANISM: Homo sapiens

<400> SEQUENCE: 1
ggagttaata gcacctcctc cgagcactcg ctcacggcgt cccccttgcct ggaaagatac    60 cgcggtccct ccagaggatt tgagggacag ggtcggaggg ggctcttccg ccagcaccgg   120
aggaagaaag aggaggggct ggctggtcac cagagggtgg ggcggaccgc gtgcgctcgg   180
cggctgcgga gaggggaga gcaggcagcg ggcggcgggg agcagcatgg agccggcggc   240
ggggagcagc atggagcctt cggctgactg gctggccacg gccgcggccc ggggtcgggt   300

<210> SEQ ID NO 2
<211> LENGTH: 22
<212> TYPE: DNA
<213> ORGANISM: Artificial sequence
<220> FEATURE:
<223> OTHER INFORMATION: primer CDKN2A-F3

<400> SEQUENCE: 2
tagaggattt gagggatagg gt                                              22

<210> SEQ ID NO 3
<211> LENGTH: 19
<212> TYPE: DNA
<213> ORGANISM: Artificial sequence
<220> FEATURE:
<223> OTHER INFORMATION: primer CDKN2A-R3

<400> SEQUENCE: 3
tacctactct cccctctc                                                   19

<210> SEQ ID NO 4
<211> LENGTH: 23
<212> TYPE: DNA
<213> ORGANISM: Artificial sequence
<220> FEATURE:
<223> OTHER INFORMATION: primer CDKN2A-F4

```
<400> SEQUENCE: 4
aggaggggtt ggttggttat tag                                             23

<210> SEQ ID NO 5
<211> LENGTH: 706
<212> TYPE: DNA
<213> ORGANISM: Homo Sapiens

<400> SEQUENCE: 5
ctgagtcttg ggtcaagtcc atcccagctc tgtcctccag gaatcaaggg aaatacgcaa     60
acccgcggtg ggttcgcagc cgcaggaagg acaaatcttg ccccgccgc ggcggccgcc    120 ccgcgttagc tgcctaagag aatctccgtg gccggccagt acccgccttg gtgaggattc   180
tccctcccgc gagaacttct ggaatgccgc cgggccagat tttgcagctg aggcctccga   240
cgccactaat attgggccaa gcaggagtg ctgctcttcc ttataaggtt ttagcgaaag    300
ttaagtaagc caattaaagt gcaaaacaca cagtctggaa caatacgcg ctctataaat    360 ggtctccatt attatcatta tccgttagtt ataactgggg ataaaaaaaa aaaaaaaacg   420
acaaaaacct ggagaaccgg aaaggtctgc aaaaggggcg gaacgcggga acttcgatt    480 ggggaagggg tggcgggga gatcccacac aagcagccaa tccagctgtc ccggggagga   540
agaggaggag tcaaggcccg cccctggtct ccgcactgct cactcccgcg cagtgaggtt   600
ggcacagcca ccgctctgtg gctcgcttgg ttcccttagt cccgagcgct cgcccactgc   660
agattccttt cccgtgcaga catggcctct ggcaccacca ccaccg                706

<210> SEQ ID NO 6
<211> LENGTH: 25
<212> TYPE: DNA
<213> ORGANISM: Artificial sequence
<220> FEATURE:
<223> OTHER INFORMATION: Forward primer for MTAP promoter

<400> SEQUENCE: 6
ggtgggttag tagtagtagg aagga                                           25

<210> SEQ ID NO 7
<211> LENGTH: 24
<212> TYPE: DNA
<213> ORGANISM: Artificial sequence
<220> FEATURE:
<223> OTHER INFORMATION: Reverse primer for MTAP promoter

<400> SEQUENCE: 7
ctccctactt aacccaatat taat                                            24
```